(12) United States Patent
Bothma et al.

(10) Patent No.: US 10,286,167 B2
(45) Date of Patent: May 14, 2019

(54) IMPELLER AND MOTOR ASSEMBLY

(75) Inventors: Johannes Nicolaas Bothma, Otorohanga (NZ); Scott Bent, Auckland (NZ); Adam John Darby, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 739 days.

(21) Appl. No.: 14/131,725

(22) PCT Filed: Jul. 13, 2012

(86) PCT No.: PCT/NZ2012/000124
§ 371 (c)(1),
(2), (4) Date: Mar. 20, 2014

(87) PCT Pub. No.: WO2013/009193
PCT Pub. Date: Jan. 17, 2013

(65) Prior Publication Data
US 2014/0216460 A1    Aug. 7, 2014

Related U.S. Application Data

(60) Provisional application No. 61/507,384, filed on Jul. 13, 2011.

(51) Int. Cl.
*A61M 16/00* (2006.01)
*F04D 29/28* (2006.01)
(Continued)

(52) U.S. Cl.
CPC ....... *A61M 16/0066* (2013.01); *F04D 17/162* (2013.01); *F04D 25/0606* (2013.01);
(Continued)

(58) Field of Classification Search
CPC .......... A61M 16/0066; A61M 5/14236; A61M 1/101; F04D 25/0606; F04D 17/08;
(Continued)

(56) References Cited

U.S. PATENT DOCUMENTS 2,929,944 A    3/1960  Shewmon
4,161,667 A    7/1979  Buckman
(Continued)

FOREIGN PATENT DOCUMENTS

CN    1266150 A    9/2000
CN    101296722 A    10/2008
(Continued)

OTHER PUBLICATIONS

International Search Report; PCT/NZ2012/000124; dated Oct. 29, 2012; 6 pages.
(Continued)

*Primary Examiner* — Timothy A Stanis
(74) *Attorney, Agent, or Firm* — Knobbe, Martens, Olson & Bear, LLP

(57) ABSTRACT

A lightweight impeller is provided for use in a pressurized gas source for a CPAP or other breathing assistance apparatus. The impeller can be shroudless or otherwise lightweight.

36 Claims, 27 Drawing Sheets

(51) Int. Cl.
| | |
|---|---|
| *F04D 29/30* | (2006.01) |
| *F04D 29/42* | (2006.01) |
| *F04D 29/66* | (2006.01) |
| *F04D 17/16* | (2006.01) |
| *F04D 25/06* | (2006.01) |
| *F04D 25/08* | (2006.01) |
| *G01F 1/075* | (2006.01) |
| *A61M 16/16* | (2006.01) |
| *F04D 27/00* | (2006.01) |

(52) U.S. Cl.
CPC ......... *F04D 25/082* (2013.01); *F04D 29/281* (2013.01); *F04D 29/30* (2013.01); *F04D 29/424* (2013.01); *F04D 29/4226* (2013.01); *F04D 29/668* (2013.01); *G01F 1/075* (2013.01); *G01F 1/0755* (2013.01); *A61M 16/0069* (2014.02); *A61M 16/16* (2013.01); *A61M 2205/42* (2013.01); *F04C 2270/041* (2013.01); *F04D 27/004* (2013.01)

(58) Field of Classification Search
CPC .... F04D 29/668; F04D 29/4226; F04D 29/30; F04D 29/281
See application file for complete search history.

(56) References Cited

U.S. PATENT DOCUMENTS

| | | | |
|---|---|---|---|
| 4,233,972 A | 11/1980 | Hauff et al. | |
| 4,357,552 A | 11/1982 | MacMillan | |
| 4,590,951 A | 5/1986 | O'Connor | |
| 5,484,270 A * | 1/1996 | Adahan | A61M 16/00 128/205.13 |
| 5,567,127 A | 10/1996 | Wentz | |
| 5,797,727 A | 8/1998 | Peters et al. | |
| 5,875,783 A | 3/1999 | Kullik | |
| 5,967,764 A | 10/1999 | Booth et al. | |
| 6,050,262 A | 4/2000 | Jay | |
| 6,376,952 B1 | 4/2002 | Stenta | |
| 6,439,861 B1 | 8/2002 | Shieh | |
| 6,543,449 B1 | 4/2003 | Woodring et al. | |
| 6,622,724 B1 * | 9/2003 | Truitt | A61M 16/00 128/204.18 |
| 6,644,310 B1 | 11/2003 | Delache et al. | |
| 6,700,255 B1 | 3/2004 | Stenta | |
| 6,717,299 B2 | 4/2004 | Bacile et al. | |
| 6,722,359 B2 | 4/2004 | Chalvignac | |
| 6,802,648 B2 | 10/2004 | Merot et al. | |
| 6,910,483 B2 | 6/2005 | Daly et al. | |
| 7,244,099 B2 | 7/2007 | Yamasaki | |
| 7,384,237 B2 | 6/2008 | Baecke et al. | |
| 7,448,383 B2 | 11/2008 | Delache et al. | |
| 7,516,743 B2 | 4/2009 | Hoffman | |
| 7,913,692 B2 | 3/2011 | Kwok | |
| 8,011,362 B2 | 9/2011 | Adams | |
| 8,020,556 B2 | 9/2011 | Shahar | |
| 8,020,557 B2 | 9/2011 | Bordewick et al. | |
| 8,042,535 B2 | 10/2011 | Kenyon et al. | |
| 8,074,645 B2 | 12/2011 | Bordewick et al. | |
| 8,074,647 B2 | 12/2011 | Truitt et al. | |
| 8,122,884 B2 | 2/2012 | Daly et al. | |
| 8,375,944 B2 | 2/2013 | Kwok | |
| D688,788 S | 8/2013 | Spruell et al. | |
| 8,638,014 B2 | 1/2014 | Sears et al. | |
| 8,973,576 B2 | 3/2015 | Kenyon | |
| 9,132,250 B2 | 9/2015 | Allum | |
| 9,132,252 B2 | 9/2015 | Barlow | |
| 2005/0188989 A1 | 9/2005 | Delache et al. | |
| 2005/0210622 A1 | 9/2005 | Baecke et al. | |
| 2006/0096596 A1 | 5/2006 | Occhialini et al. | |
| 2006/0237013 A1 | 10/2006 | Kwok | |
| 2007/0017518 A1 | 1/2007 | Farrugia et al. | |
| 2007/0251527 A1 | 11/2007 | Sleeper | |
| 2007/0277827 A1 | 12/2007 | Bordewick et al. | |
| 2007/0284952 A1 | 12/2007 | Ihle | |
| 2008/0149306 A1 | 6/2008 | Hwang et al. | |
| 2008/0178879 A1 | 7/2008 | Roberts et al. | |
| 2008/0216835 A1 | 9/2008 | McGinnis et al. | |
| 2008/0304986 A1 * | 12/2008 | Kenyon | A61M 16/0066 417/423.12 |
| 2009/0071480 A1 * | 3/2009 | Adams | A61M 16/0066 128/204.18 |
| 2009/0194101 A1 | 8/2009 | Kenyon | |
| 2009/0301485 A1 | 12/2009 | Kenyon et al. | |
| 2009/0315492 A1 * | 12/2009 | Oomura | H02P 6/20 318/400.02 |
| 2009/0320842 A1 | 12/2009 | Doherty | |
| 2010/0059055 A1 * | 3/2010 | Brungart | A61M 16/0066 128/204.18 |
| 2010/0059056 A1 | 3/2010 | Sears et al. | |
| 2010/0132711 A1 * | 6/2010 | Kenyon | A61M 16/0057 128/205.25 |
| 2010/0170513 A1 | 7/2010 | Bowditch et al. | |
| 2011/0073110 A1 | 3/2011 | Kenyon | |
| 2011/0132363 A1 | 6/2011 | Chalvignac | |
| 2012/0000463 A1 | 1/2012 | Bordewick et al. | |
| 2012/0080032 A1 | 4/2012 | Bordewick et al. | |
| 2012/0097156 A1 | 4/2012 | Bowman et al. | |
| 2012/0138058 A1 | 6/2012 | Fu et al. | |
| 2012/0152255 A1 | 6/2012 | Barlow et al. | |
| 2012/0167879 A1 | 7/2012 | Bowman | |
| 2012/0266873 A1 | 10/2012 | Lalonde | |
| 2012/0285454 A1 * | 11/2012 | Nibu | A61M 16/0066 128/204.18 |
| 2013/0098359 A1 | 4/2013 | Becker et al. | |
| 2013/0152918 A1 | 6/2013 | Rummery | |
| 2013/0306072 A1 | 11/2013 | Moir | |
| 2014/0227091 A1 | 8/2014 | Kenyon et al. | |
| 2015/0157818 A1 | 6/2015 | Darby et al. | |
| 2015/0328418 A1 | 11/2015 | Bothma et al. | |

FOREIGN PATENT DOCUMENTS

| | | |
|---|---|---|
| CN | 101321958 A | 12/2008 |
| CN | 101449064 A | 6/2009 |
| CN | 101466429 A | 6/2009 |
| DE | 3310376 A1 | 9/1984 |
| EP | 1035330 B1 | 9/2000 |
| EP | 1205203 A2 | 5/2002 |
| EP | 1205203 B1 | 5/2002 |
| EP | 1205203 A3 | 7/2002 |
| EP | 1205203 B1 | 9/2004 |
| EP | 2317150 A1 | 5/2011 |
| GB | 1041313 A | 9/1966 |
| JP | 2002-511786 A | 4/2002 |
| JP | 2004-353655 A | 12/2004 |
| JP | 2007-506482 A | 3/2007 |
| WO | WO 2007/048206 A1 | 5/2007 |
| WO | WO 2007/134405 A1 | 11/2007 |
| WO | WO 2008/028247 | 3/2008 |
| WO | WO 2008/092235 A1 | 8/2008 |
| WO | WO 2010/028121 | 3/2010 |
| WO | WO 2010/096467 A1 | 8/2010 |
| WO | WO 2011/017763 A1 | 2/2011 |
| WO | WO 2011/022779 A1 | 3/2011 |
| WO | WO 2011/062633 | 5/2011 |
| WO | WO 2011/112807 | 9/2011 |
| WO | WO 2012/024740 | 3/2012 |
| WO | WO 2012/094230 | 7/2012 |
| WO | WO 2012/113027 | 8/2012 |
| WO | WO 2012/145358 A2 | 10/2012 |
| WO | WO 2012/174602 | 12/2012 |
| WO | WO 2013/020167 | 2/2013 |

OTHER PUBLICATIONS

Written Opinion; PCT/NZ2012/000124; dated Oct. 29, 2012; 9 pages.
European Search Report; dated Jul. 20, 2015; 13 pages.
China First Office Action; 201280034511.4; dated Jul. 29, 2015; 28 pages.

(56) References Cited

OTHER PUBLICATIONS

China First Office Action; 201380018302.5; dated Nov. 4, 2015; 9 pages.
International Search Report; PCT/IB2013/060549; dated Mar. 19, 2014; 5 pages.
Written Opinion; PCT/IB2013/060549, dated Mar. 19, 2014; 6 pages.
Japanese Examination Report with English Translation, dated Dec. 19, 2016; 8 pages.
Sep. 24, 2013 International Search Report and Written Opinion for Application No. PCT/NZ2013/000006 dated on Feb. 1, 2013.
Sep. 24, 2013 Written Opinion for Application No. PCT/NZ2013/000006 dated on Feb. 1, 2013.
Extended European Search Report for European Patent Application No. 17157168.0, dated Jun. 12, 2017, in 7 pages.
Examination Report for Australian Application No. 2017204037, dated Nov. 16, 2017; 3 pages.
Examination Report No. 2 for Australian Application No. 2017204037, dated Jan. 3, 2018; 2 pages.

\* cited by examiner

IMPELLER AND MOTOR ASSEMBLY

CROSS-REFERENCE TO RELATED APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This invention relates to a gases supply and gases humidification apparatus, particularly but not solely for providing respiratory assistance to patients or users who require a supply of gas for the treatment of diseases such as Obstructive Sleep Apnea (OSA), snoring, or Chronic Obstructive Pulmonary Disease (COPD) and the like. In particular, this invention relates to a compressor or blower for use in a gases supply apparatus which in use is integral with the gases supply apparatus.

Description of the Related Art

Devices or systems for providing a humidified gases flow to a patient for therapeutic purposes are well known in the art. Systems for providing therapy of this type, for example CPAP therapy, have a structure where gases at the required pressure are delivered from a blower (also known as a compressor, an assisted breathing unit, a fan unit, a flow generator or a pressure generator) to a humidifier chamber downstream from the blower. As the gases are passed through the heated, humidified air in the humidifier chamber, they become saturated with water vapour. The gases are then delivered to a user or patient downstream from the humidifier, via a gases conduit.

Humidified gases can be delivered to a user from a modular system that has been assembled from separate units (that is, a system where the humidifier chamber/heater and the breathing unit/blower are separate items) connected in series via conduits. A schematic view of a user 1 receiving air from a modular assisted breathing unit and humidifier system (together or separately a "breathing assistance apparatus") is shown in FIG. 1. Pressurised air is provided from an assisted breathing unit or blower 2a via a connector conduit 10 to a humidifier chamber 4a. Humidified, heated and pressurised gases exit the humidifier chamber 4a via a user conduit 3, and are provided to the patient or user 1 via a user interface 5.

It is becoming more common for integrated blower/humidifier systems to be used. A typical integrated system ("breathing assistance apparatus") consists of a main blower or assisted breathing unit which provides a pressurised gases flow, and a humidifier unit that mates with or is otherwise rigidly connected to the blower unit. This mating occurs for example by a slide-on or push connection, so that the humidifier is held firmly in place on the main blower unit. A schematic view of the user 1 receiving air from an integrated blower/humidifier unit 6 is shown in FIG. 2. The system operates in the same manner as the modular system shown in FIG. 1, except that humidifier chamber 4b has been integrated with the blower unit to form the integrated unit 6.

The user interface 5 shown in FIGS. 1 and 2 is a nasal mask, covering the nose of the user 1. However, it should be noted that in systems of these types, a mask that covers the mouth and nose, a full face mask, a nasal cannula, or any other suitable user interface could be substituted for the nasal mask shown. A mouth-only interface or oral mask could also be used. Also, the patient or user end of the conduit can be connected to a tracheostomy fitting, or an endotracheal intubation.

U.S. Pat. No. 7,111,624 includes a detailed description of an integrated system. A 'slide-on' water chamber is connected to a blower unit in use. A variation of this design is a slide-on or clip-on design where the chamber is enclosed inside a portion of the integrated unit in use. An example of this type of design is shown in WO 2004/112873, which describes a blower, or flow generator 50, and an associated humidifier 150.

For these systems, the most common mode of operation is as follows: air is drawn by the blower through an inlet into the casing which surrounds and encloses at least the blower portion of the system. The blower (controlled by a microcontroller, microprocessor or similar) pressurises the air stream from the flow generator outlet and passes this into the humidifier chamber. The air stream is heated and humidified in the humidifier chamber, and exits the humidifier chamber via an outlet. A flexible hose or conduit is connected either directly or indirectly to the humidifier outlet, and the heated, humidified gases are passed to a user via the conduit. This is shown schematically in FIG. 2.

Impeller type fans or blowers are most commonly used in breathing systems of this type. An impeller blade unit is contained within an impeller housing. The impeller blade unit is connected to a drive of some form by a central spindle 55. A typical impeller housing is shown in FIGS. 3 and 4. A typical rotating impeller unit 154, having a plurality of blades 151 and a shroud 152, which in use is located inside the housing is shown in FIGS. 5 and 6. Air is drawn into the centre of the impeller unit through an aperture, and is then forced outwards from the centre of the housing towards an exit passage (usually located to one side of the housing) by the blades of the rotating impeller unit.

Generally, domestic users receive treatment for sleep apnea or similar. It is most common for a nasal mask, or a mask that covers both the mouth and nose, to be used. If a nasal mask is used, it is common to strap or tape the mouth closed, so that the use of the system is effective (mouth leak and the associated pressure drop are substantially reduced or eliminated). For the range of flows dictated by the user's breathing, the CPAP device pressure generator provides a flow of gases at a substantially constant pressure. The pressure can usually be adjusted before use, or during use, either by a user, or a medical professional who sets up the system. Systems that provide variable pressure during use are also known—for example BiPAP machines that provide two levels of pressure: One for inhalation (IPAP) and a lower pressure during the exhalation phase (EPAP). Variable pressure or constant pressure systems are all "breathing assistance apparatus"

SUMMARY OF THE INVENTION

It is an object of the present invention to provide an improved impeller or blower/compressor for use with a breathing assistance apparatus or an improved breathing assistance apparatus.

In one aspect the present invention may be said to consist in a breathing assistance apparatus comprising: a pressurised gases source comprising: a gases inlet, a gases outlet adapted to emit pressurised gases to an outlet of the breathing assistance apparatus, and a lightweight impeller.

Preferably lightweight impeller is shroudless or otherwise has reduced material.

Preferably lightweight impeller is formed in one piece.

Preferably the lightweight impeller has a radius of between 15 and 60 mm.

Preferably the lightweight impeller has a mass of less than 2 grams and preferably between 0.8 and 1.8 grams.

Preferably the lightweight impeller has a pressure to inertia to radius ratio greater than 50:1 Pa per gram*mm, and preferably greater than 80:1 Pa per gram*mm.

Preferably the lightweight impeller has a moment of inertia to radius ratio less than 15 g*mm and preferably within the range of 8 to 12 g*mm.

Preferably the lightweight impeller has a blade sweep volume to a blade volume ratio of 16:1 or greater.

Preferably the impeller is a centrifugal impeller rotatable about a central axis.

Preferably the breathing assistance apparatus comprises a motor for driving the impeller wherein the motor is operated using field oriented control.

Preferably the gases source further comprises a housing having upper and lower internal surfaces that enclose the impeller, and wherein the impeller has a plurality of blades that are substantially open to the upper and lower internal surfaces of the housing by virtue of being shroudless.

Preferably the housing forms part of or is integrated with the breathing assistance apparatus.

Preferably the gases source further comprises a partition to define first and second interior regions within the housing, wherein the first and second regions are fluidly connected by an opening formed in or by the partition.

Preferably the opening formed in or by the partition is at least partially circumferential.

Preferably opening formed in or by the partition is crescent shaped.

Preferably the first region is defined by the housing and the partition and comprises the gases inlet.

Preferably the second region is defined by the housing and the partition and comprises the gases outlet.

Preferably the impeller has an axis of rotation, the partition extending radially from the axis of rotation.

Preferably the housing further comprises a volute in the second region.

Preferably the opening is proximate the periphery of the volute.

Preferably the impeller is located within the first region.

Preferably a distal end of the impeller blades curve in the direction of blade rotation.

Preferably the breathing assistance apparatus further comprises a motor, the motor comprising: a rotatable shaft located within a stator, and at least one bearing structure to support the rotatable shaft within the stator, the bearing structure having one or more bearing mounts.

Preferably the bearing mount provides compliant support to the rotatable shaft.

Preferably an outer portion of the one or more bearing mounts engages the stator and/or a stator frame and/or other structure.

Preferably an outer portion of the one or more bearing mounts engages the stator and/or frame of the stator.

Preferably the stator comprises a stator frame, an inner surface of the stator frame engages with the bearing structure.

Preferably the bearing structure further comprises one or more bearings supported by the bearing mounts about the axis of the rotatable shaft.

Preferably the pressurised gases source has a housing and the breathing apparatus further comprises a motor mount that couples the stator and the housing to provide compliant support to the motor.

Preferably the bearing mount and/or motor mount are flexible and/or resilient.

Preferably the volute has a tongue at least partially defining a transition between the volute and the gases outlet, the tongue located in the second interior region.

Preferably the bearing mounts have a curved annular body and when engaged with the stator and/or stator frame and/or other structure the annular body is coerced into an engaged configuration that provides preload to the one or more bearings.

Preferably the bearing mount is made from a material that provides resilience and/or flexibility to provide preload when in the engaged configuration.

Preferably the bearing mounts are made from a material that provides damping.

Preferably the motor is operated using field oriented control.

In another aspect the present invention may be said to consist in a breath assistance apparatus comprising: a motor comprising a rotatable shaft located within a stator, a bearing structure to support the rotatable shaft in the stator, the bearing structure having one or more bearing mounts.

Preferably the bearing mounts provide compliant support to the rotatable shaft.

Preferably an outer portion of the one or more bearing mounts engages the stator and/or a stator frame and/or other structure.

Preferably the stator comprises a stator frame, an inner surface of the stator frame engaging with the bearing structure.

Preferably the bearing structure further comprises one or more bearings supported by the bearing mounts about the axis of the rotatable shaft.

Preferably the bearing mount is flexible and/or resilient.

Preferably the bearing mounts have a curved annular body and when engaged with the stator and/or stator frame and/or other structure the annular body is coerced into an engaged configuration that provides preload to the one or more bearings.

Preferably the bearing mount is made from a material that provides resilience and/or flexibility to provide preload when in the engaged configuration.

Preferably the bearing mounts are made from a material that provides damping.

In another aspect the present invention may be said to consist in a pressurised gases source comprising: a centrifugal impeller driven by a motor within a housing, the housing having a gases inlet, a gases outlet and a partition to define first and second interior regions wherein the first and second regions are fluidly connected by an opening in the partition.

Preferably the first region is defined by the housing and the partition and comprises the gases inlet.

Preferably the second region is defined by the housing and the partition and comprises the gases outlet.

A pressurised gases source according to any of the above used in a breathing assistance apparatus according to any of the above.

In another aspect the present invention may be said to consist in a breathing assistance apparatus comprising: a pressurised gases source comprising: a housing a gases inlet, a gases outlet adapted to emit pressurised gases to an outlet of the breathing assistance apparatus, a motor with a rotatable shaft and at least one bearing structure to support the rotatable shaft within a stator, the bearing structure having one or more flexible and/or resilient bearing mounts to provide compliance and/or preload and/or damping for the rotatable shaft, a lightweight impeller coupled to the rotatable shaft, a flexible and/or resilient motor mount that couples the stator and the housing to provide compliance and/or damping for the motor a partition to define first and second interior regions within the housing, wherein the first and second regions are fluidly connected by a crescent shaped opening formed in or by the partition.

Preferably the lightweight impeller is shroudless or otherwise has reduced material.

Preferably the lightweight impeller is formed in one piece.

Preferably the lightweight impeller has a radius of between 15 and 60 mm.

Preferably the lightweight impeller has a mass of less than 2 grams and preferably between 0.8 and 1.8 grams.

Preferably the lightweight impeller has a pressure to inertia to radius ratio greater than 50:1 Pa per gram*mm, and preferably greater than 80:1 Pa per gram*mm.

Preferably the lightweight impeller has a moment of inertia to radius ratio less than 15 g*mm and preferably within the range of 8 to 12 g*mm.

Preferably the lightweight impeller has a blade sweep volume to a blade volume ratio of 16:1 or greater.

In another aspect the present invention may be said to consist in a pressurised gases source comprising: a gases inlet, a gases outlet, a motor with a shaft, and a lightweight impeller connected to the motor and rotatable to draw gases from the inlet and emit gases through the outlet, wherein the impeller is shroudless or otherwise has reduced material.

Preferably the impeller is a centrifugal impeller rotatable about a central axis.

Preferably the gases source further comprises a housing having upper and lower internal surfaces that enclose the impeller, and wherein the impeller has a plurality of blades that are substantially open to the upper and lower internal surfaces of the housing by virtue of being shroudless.

Preferably the housing forms part of or is integrated with a CPAP machine.

Preferably the gases source further comprises a partition to define first and second interior regions within the housing, wherein the first and second regions are fluidly connected by an opening formed in or by the partition.

Preferably the opening formed in or by the partition is at least partially circumferential.

Preferably the first interior region is defined by the housing and the partition and comprises the gases inlet.

Preferably the second interior region is defined by the housing and the partition and comprises the gases outlet.

Preferably the impeller has an axis of rotation, the partition extending radially from the axis of rotation.

Preferably the housing further comprises a volute in the second region.

Preferably the opening is proximate the periphery of the volute.

Preferably the impeller is located within the first region.

Preferably a distal end of the impeller blades curve in the direction of blade rotation.

Preferably the further comprising a motor, the motor comprising: a rotatable shaft located within a stator, and at least one bearing structure to support the rotatable shaft, the bearing structure having one or more bearing mounts engaged and axially aligned with the stator to provide compliant support to the rotatable shaft.

Preferably an outer portion of the one or more bearing mounts engages the stator.

Preferably the stator comprises a stator frame, an inner surface of the stator frame engaging with the bearing structure.

Preferably the bearing structure further comprises one or more bearings supported by the bearing mounts about the axis of the rotatable shaft.

Preferably the pressurised gases source further comprises a motor mount that couples the stator frame and the housing to provide compliant support to the motor.

Preferably the bearing mount is flexible and/or resilient.

Preferably the volute has a tongue at least partially defining a transition between the volute and the gases outlet, the tongue located in the second interior region.

Preferably the motor is vector controlled.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

BRIEF DESCRIPTION OF THE DRAWINGS

A preferred form of the present invention will now be described with reference to the accompanying drawings.

DETAILED DESCRIPTION OF THE PREFERRED EMBODIMENT

The present invention will be described with reference to a breathing assistance apparatus/system where the humidifier chamber is integrated with the gases supply unit (also referred to as a respirator unit or blower unit). However, it should be noted that the system is equally applicable to a modular system.

The present invention relates to a lightweight/low inertia impeller. The lightweight nature of the impeller provides low inertia.

Figure 7:
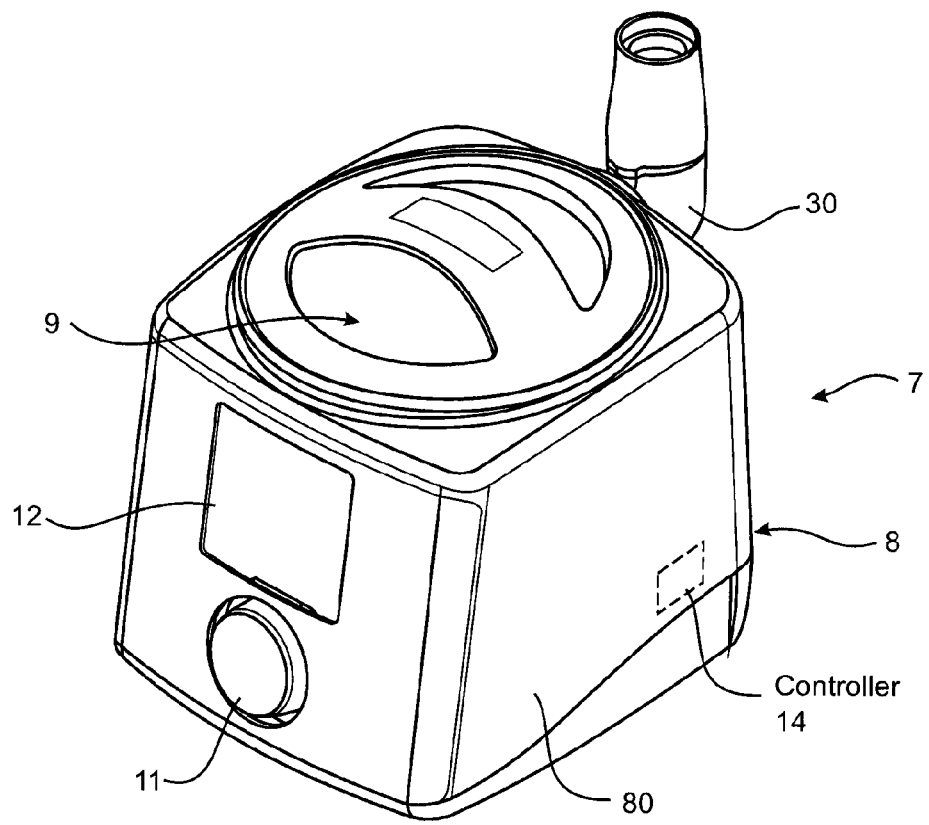
FIG. 7 shows a profiled view of a gases supply unit.

An example of an integrated gases supply unit 7 with which embodies the present invention is shown in FIG. 7—this is one example and should not be limiting. The integrated unit 7 comprises two main parts: a gases supply unit or blower unit 8 and a humidifier unit 9. Humidification unit 9 is partially enclosed within the external shell 80 of the blower unit 8 in use, except for the top of the humidification unit 9. It also comprises an internal controller 14 such as a microcontroller, microprocessor or similar for controlling the blower unit and other operations, such as that shown schematically in dotted lines. It is not necessary to describe the structure and operation of the humidification unit 9 in detail in order to fully describe the present invention.

The body of the gases supply unit 8 has the form of a generally rectangular block with substantially vertical side and rear walls, and a front face that is angled slightly rearwards (all the walls can be angled inwards slightly if required). In the preferred embodiment, the walls, base and top surface are all manufactured and connected as far as possible to minimise the occurrence of seams, and any necessary seams are sealed. As shown in FIG. 7, the gases supply unit 8 includes a control knob 11, located on the lower section of the front face of the gases supply unit 8, with a control display 12 located directly above the knob 11. A patient outlet 30 is shown passing out of the rear wall of the gases supply unit 8. In the preferred embodiment, the free end of the outlet 30 faces upwards for ease of connection. The patient outlet 30 is adapted to allow both pneumatic and electrical connection to one end of a conduit—e.g. conduit 3—running between the integrated unit 7 and a patient interface—e.g. interface 5. An example of the type of connector that can be used and the type of dual connection that can be made is described in U.S. Pat. No. 6,953,354. It should be noted that for the purposes of reading this specification, the patient interface can be thought of as including both the interface 5 and the conduit 3 where it would be appropriate to read it in this manner.

Figure 8:
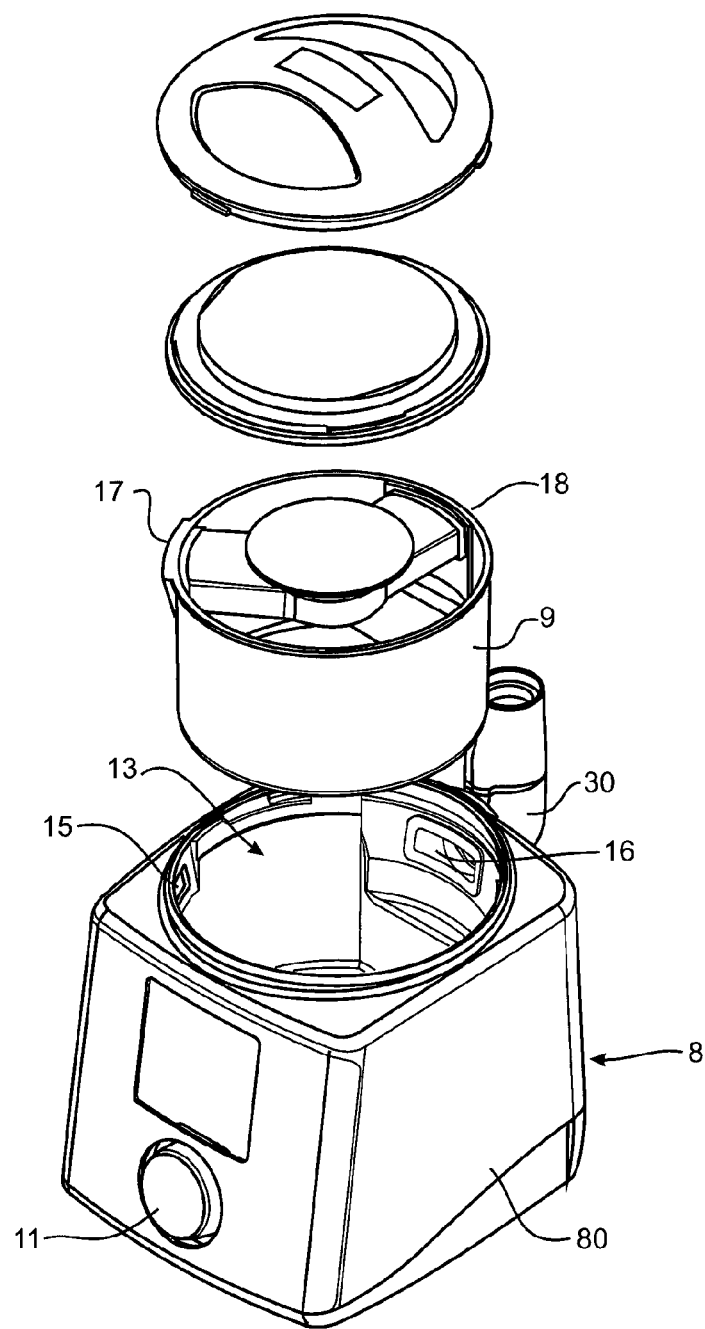
FIG. 8 shows an exploded view of the gases supply unit of FIG. 7.
Figure 9:
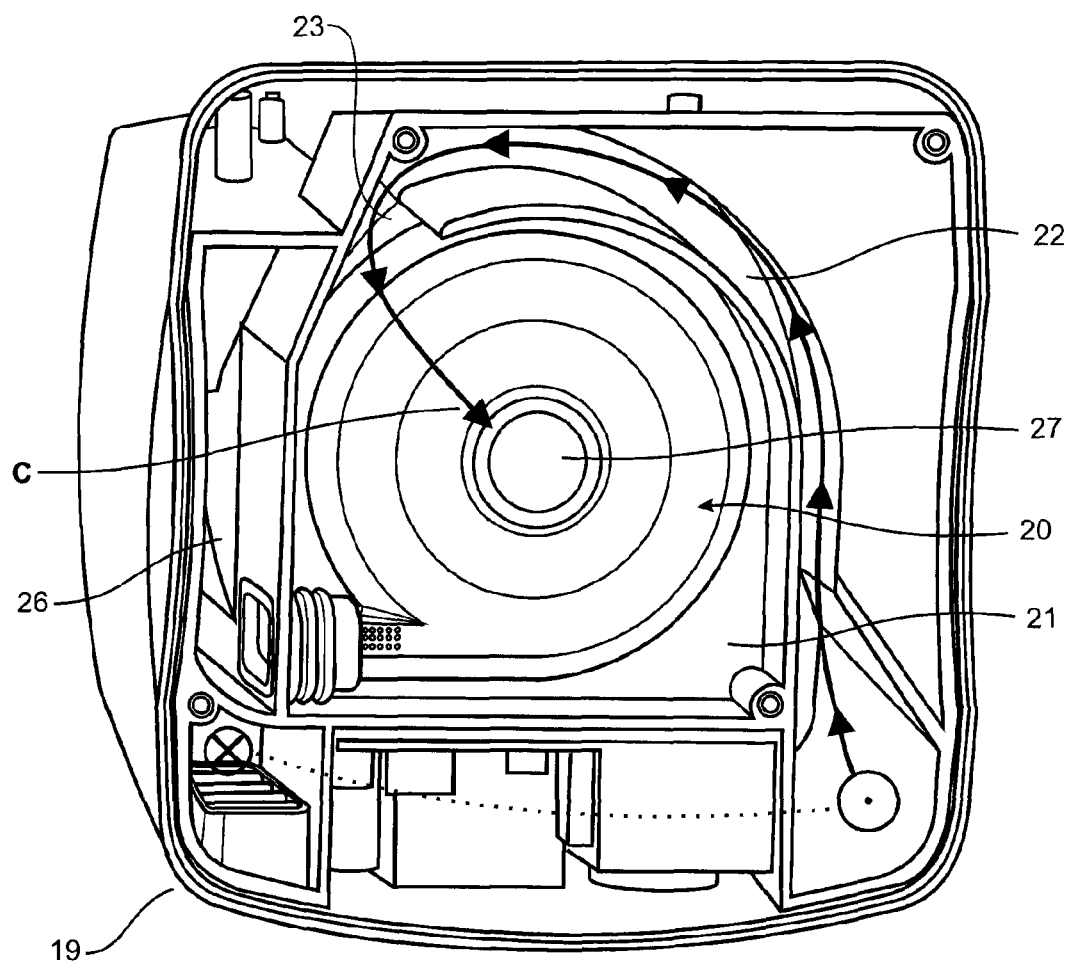
FIG. 9 shows an internal view of a gases supply unit (viewed from underneath).
Figure 10:
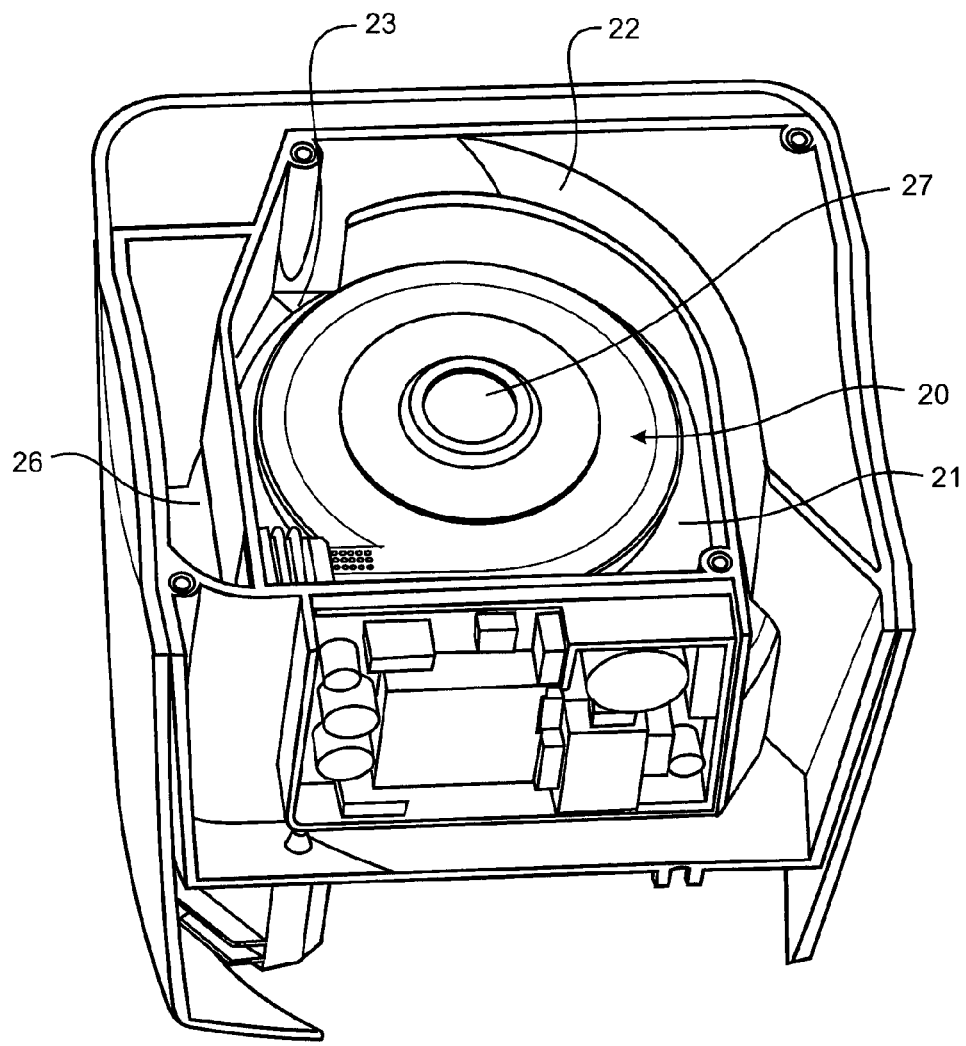
FIG. 10 shows a profiled view of the gases supply unit of FIG. 9.

The internal structure and components of the gases supply unit 8 will now be described with reference to FIGS. 8, 9 and 10. The gases supply unit 8 includes an enclosing external shell 80 which forms part of, and encloses, the gases supply unit 8. The shell 80 includes internal air passages for ducting air passing through the gases supply unit 8, and also internal recesses, cavities or slots into which components of the gases supply unit 8 is located in use. The shell 80 of the gases supply unit 8 is further adapted to include an open-topped compartment 13. In use, humidifier chamber 9 is located within the compartment 13. Blower unit 8 includes a heater base or heater plate, located at the bottom of the compartment 13. A humidifier inlet aperture 15 and humidifier outlet aperture 16 are located on the wall of the compartment 13, towards the top of the compartment 13. In the preferred embodiment, the inlet and outlet apertures 15, 16 are aligned so as to mate with inlet and outlet humidifier ports 17, 18 located on the humidifier chamber 9, when the system is in use. It should be noted that other forms of humidifier inlet are possible. For example, a conduit running between the gases supply unit 8 and e.g. the lid of the humidifier chamber 9. Also, if the humidifier chamber is a separate item (that is, not rigidly connected to the gases supply unit in use), the humidifier inlet aperture 15 will not be connected directly to the humidifier chamber, but will be connected instead to one end of a conduit or similar leading from the humidifier inlet aperture on the gases supply unit, to the humidifier chamber.

Air from atmosphere is drawn into the shell of the gases supply unit 8 through an atmospheric inlet vent 19. This vent 19 can be located wherever is convenient on the external surface of the shell of the gases supply unit 8. In the preferred embodiment, as shown in FIG. 9 (viewing the housing from underneath), the inlet vent 19 is located on the rear face of the shell of the gases supply unit 8, on the right hand side of the rear face (right hand side when looking forwards). In the preferred embodiment, air is drawn in through the inlet vent 19 by means of a fan unit 20 which forms part of the gases supply unit 8, and which is located inside the enclosing external shell of the gases supply unit 8. The fan unit 20 provides a pressurised gases stream for the gases supply unit and therefore the assisted breathing system. The fan unit 20 will be described in more detail below. The air is drawn into the fan unit 20 indirectly, via a curved inlet path 22 formed through the shell of the gases supply unit 8. Path C runs from the inlet vent 19 up over the power supply cavity and though the venturi (shown in dotted lines) past into curved path 22 (including absorber foam channel and through a thermistor flow sensor) to an aperture 23 formed in the gases supply unit shell 80, the aperture 23 passing into a recess/plenum 21 which is formed in the gases supply unit shell 80, in which the fan unit 20 is located. The air then passes into the inlet 27.

The gases stream passes through the fan unit 20 to the humidifier inlet aperture 15 as follows: the shell of the gases supply unit 8 includes a chamber or outlet duct 26 which forms at least part of an outlet air path to allow gaseous communication between the fan unit 20 and the humidifier inlet aperture 15. In the preferred embodiment, the outlet duct 26 runs up between the right hand side wall of the gases supply unit 8 (from behind looking forwards) and the front wall, up to the humidifier inlet aperture 15. As shown in FIGS. 9 and 10, air exiting the fan unit 20 enters the duct 26.

In use, air exits the shell of the gases supply unit or blower 8 via the humidifier inlet aperture 15 and enters the humidifier chamber 9. In the preferred form, the humidifier inlet aperture 15 forms an outlet at the end of the duct 26. The gases are humidified and heated in the chamber 9, before passing out of the chamber 9 through the humidifier outlet aperture 16, which is directly or indirectly connected to the patient outlet 30 (it should be noted that the outlet of the humidifier chamber 9 could also be completely separate from the gases supply unit 8). The heated humidified gas is then passed to the user 1 via conduit 3. The patient outlet 30 is adapted to enable pneumatic attachment of the patient conduit 3, and in the preferred embodiment, outlet 30 is also adapted to enable electrical connection via an electrical connector. A combined electrical and pneumatic connection can be useful for example if the conduit 3 is to be heated. Electrical heating of a conduit such as conduit 3 can prevent or minimise the occurrence of condensation within the conduit 3. It should also be noted that the outlet connection does not have to be via the shell of the integrated unit 7. If required, the connection for the conduit 3 could be located directly on an outlet from humidifier chamber 9.

The blower unit 8 in use is set to a user-specified pressure level and/or the pressure level can be automatically controlled. The flow rate for the preferred embodiment will vary during use, depending on the users breathing. The power to fan unit 20 can be altered, to change the speed at which the impeller 24 is rotating, and therefore the pressure.

The structure of the fan unit 20 according to one embodiment shall now be described, with particular reference to FIGS. 11, 12 and 13. The fan unit 20 is located in recess 21 of the shell of the gases supply unit 8 in use, as described above with reference to FIGS. 9 and 10. In the preferred form, the fan unit 20 comprises a rotating impeller located inside a casing having the form of a snail or scroll casing 25.

Figure 11:
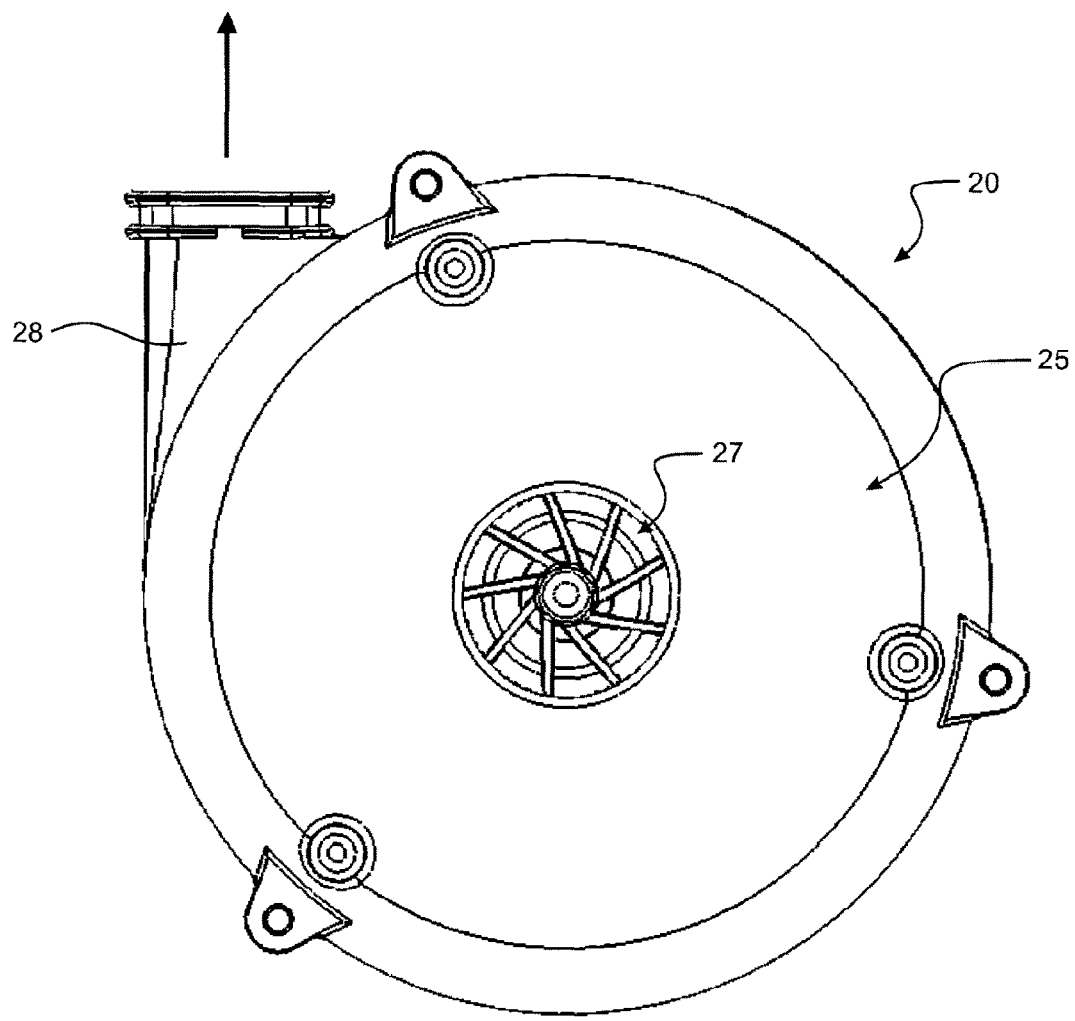
FIG. 11 shows a plan view of the top side of a blower unit of one embodiment.
Figure 12:
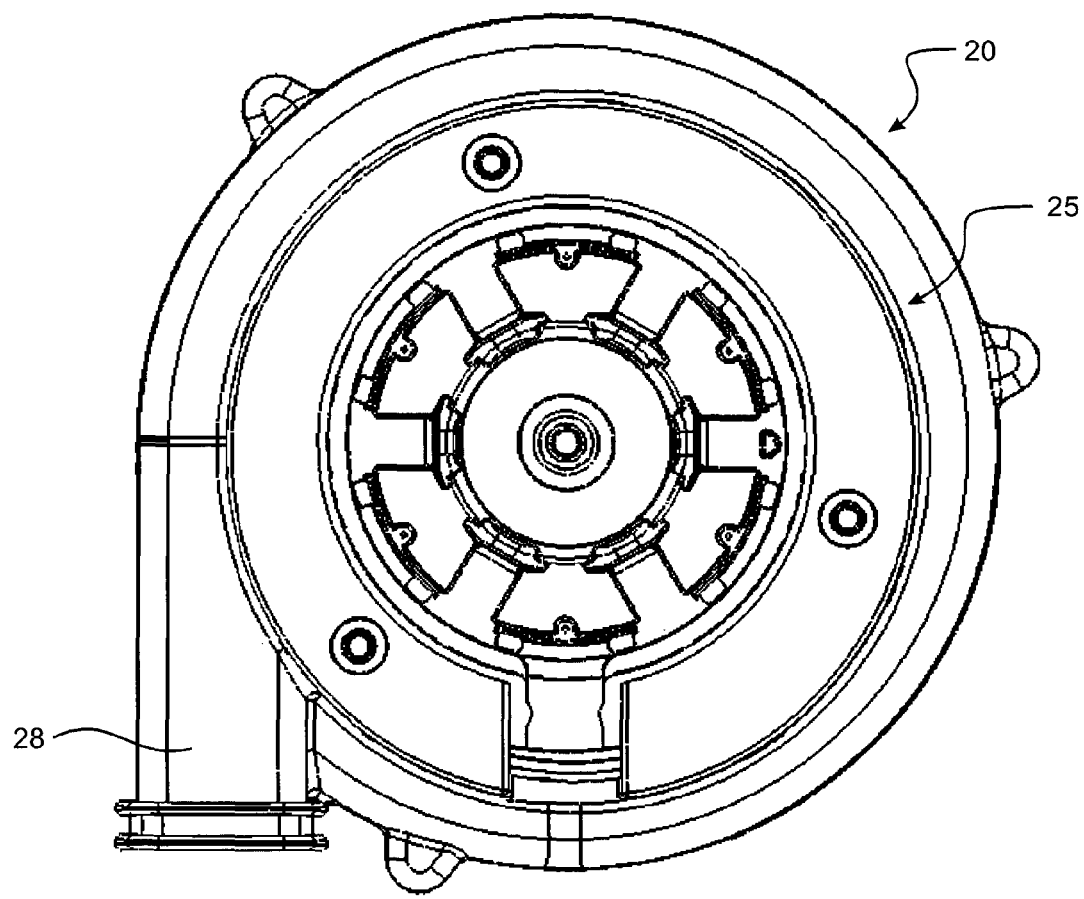
FIG. 12 shows a plan view of the bottom side of the blower unit of FIG. 11.
Figure 13:
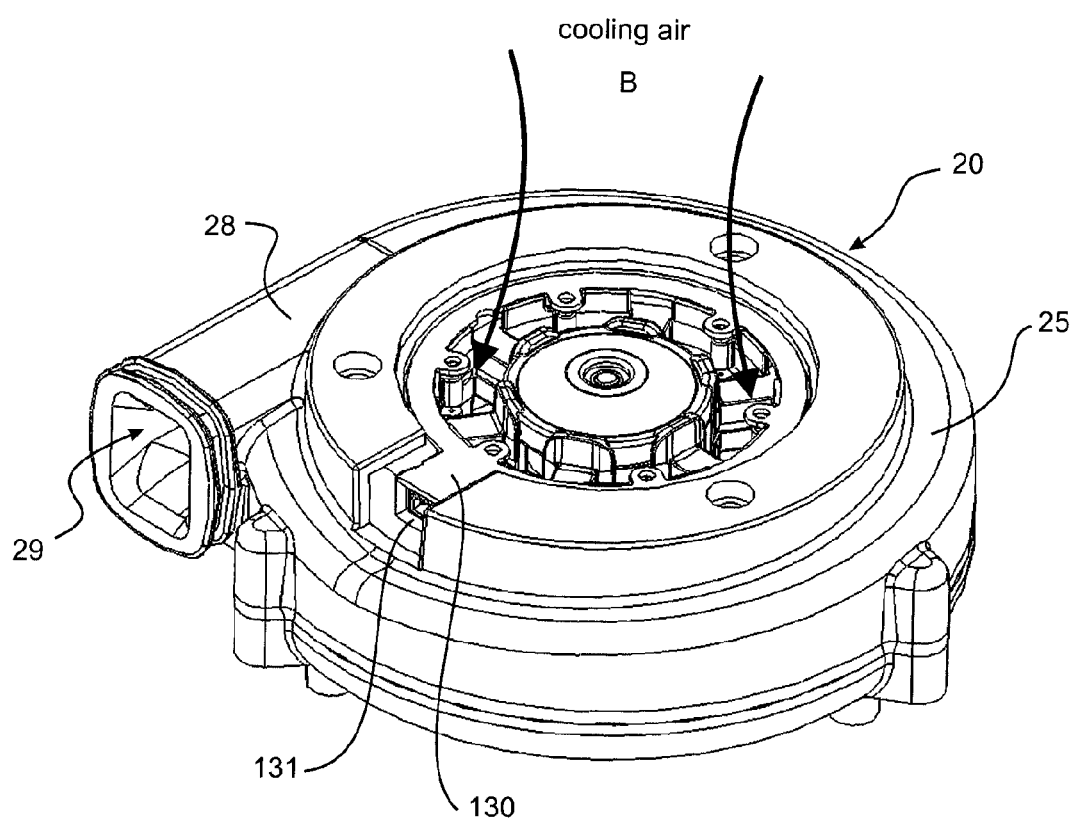
FIG. 13 shows a profile view of the bottom side of the blower unit of FIG. 12

It can be seen that the fan unit 20 appears generally circular in plan view, as shown in FIGS. 11 and 12. The fan casing 25 includes an inlet aperture 27. In the preferred form, inlet aperture 27 is a circular hole located in approximately the centre of the casing 25 and passing from the outside of the casing to the inside. Air from the inlet path 22 (see FIG. 10) enters the fan casing 25 via the inlet aperture 27. It should be noted that where it would be appropriate to include the aperture 23 and at least part of the recess 21 as part of the air inlet path, the specification should be read as including these elements. The preferred form of the casing 25 of the fan unit 20 also includes an outlet passage 28.

In the preferred form, the outlet passage 28 is a short passage formed as an integral part of the casing 25 and aligned substantially tangentially to the circumference to the remainder of the generally circular casing 25. A fan casing outlet aperture or exit aperture 29 (see e.g. FIG. 13) is located at the outer end of the passage 28. It should be noted that the fan casing exit aperture 29 could be located wherever is convenient on the passage 28 (i.e. it does not have to be at the end of the passage, it could be through the passage wall partway along its length, for example). Exit aperture 29 opens into the duct 26. The outlet passage 28 forms part of the air path from the fan to the humidifier inlet aperture 15.

The fan casing 25 encloses the fan in use, except for the inlet aperture 27 and the exit aperture 29 of the passage 28. In the preferred embodiment, rotation of the fan unit 20 is driven by a motor, the fan or impeller unit being adapted for connection to the motor. Air or gases are drawn through inlet aperture 27 in the centre of the casing 25, into the centre of the impeller unit 24, and are then forced outwards as a gases stream through the exit aperture 29 of the outlet passage 28 by the impeller blades 31 as the impeller unit 24 rotates.

In the preferred form, the fan outlet passage or exit passage 28 has a generally rectangular cross-section, and the exit passage 28 is aligned substantially tangentially to the casing 25. However, the cross-section of the fan outlet passage 28 could be any suitable shape, such as oval, rectangular or circular. The fan outlet passage 28 could also be arranged at any suitable angle to the impeller unit, for example facing radially outwards, or at any suitable angle between tangential and radial. The fan outlet passage 28 causes the gases forced outwards by the impeller unit 24 to coalesce as a fluidic gases stream, and dictates the direction in which the gases stream flows. The overall path or overall direction of the gases flow will be along the passage from the fan towards the fan casing exit aperture 29.

Figure 1:
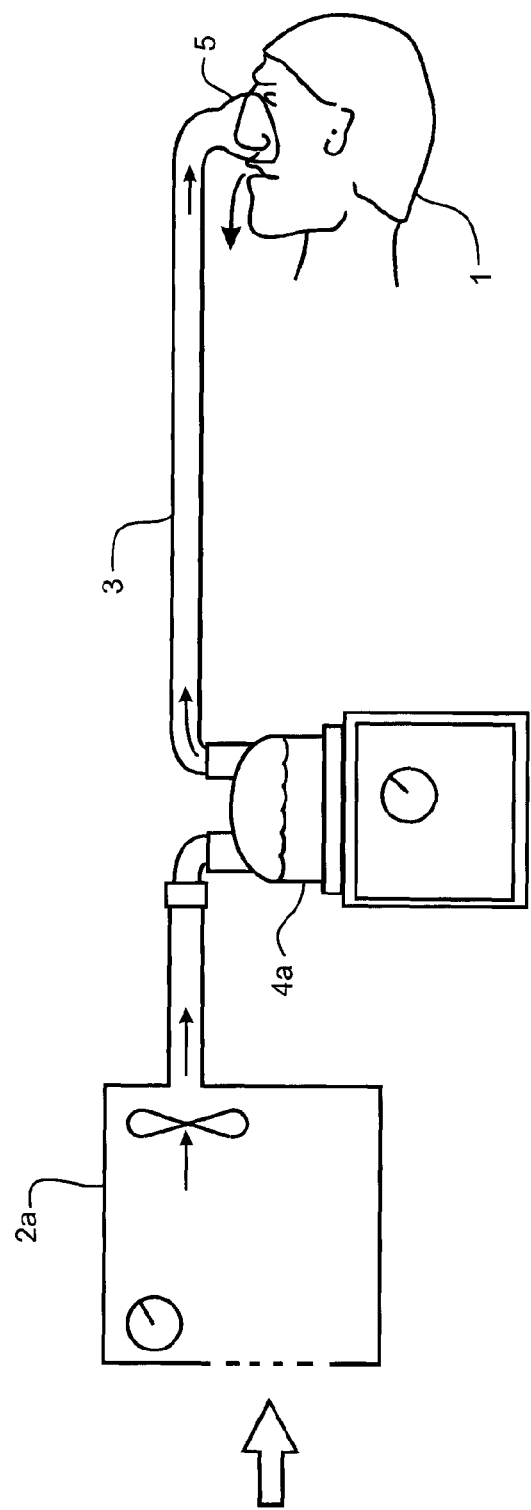
FIG. 1 shows a schematic view of a modular assisted breathing unit and humidifier system.
Figure 2:
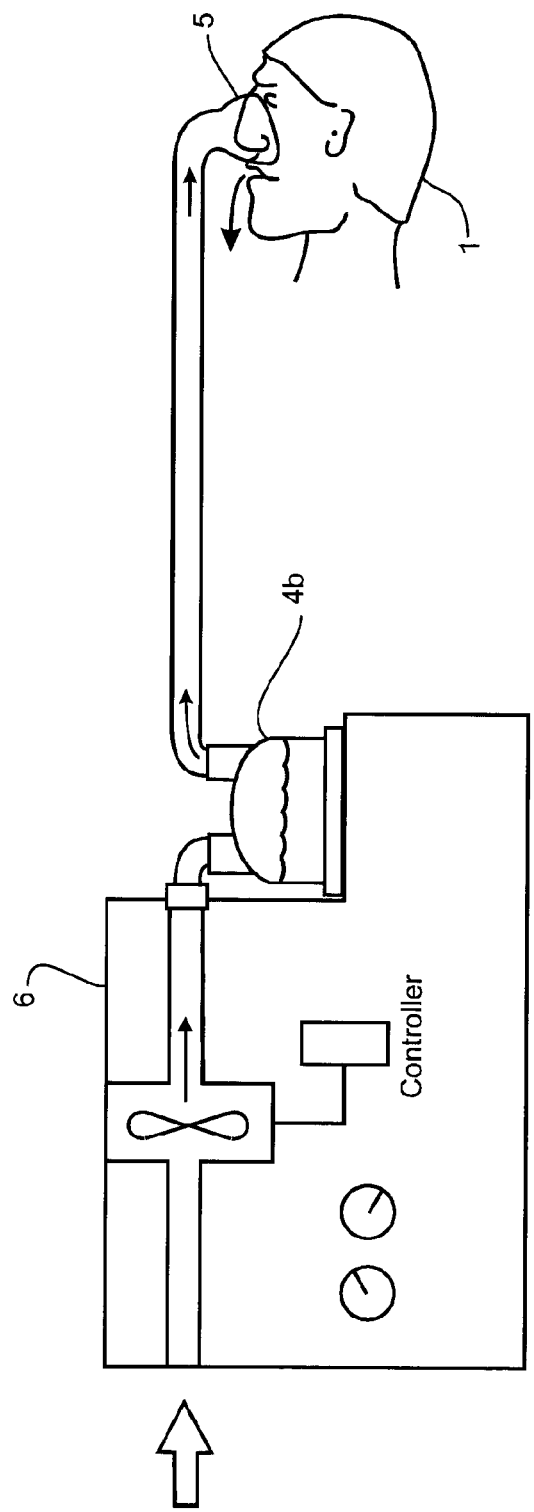
FIG. 2 shows a schematic view of a modular assisted breathing unit and humidifier system.
Figure 3:
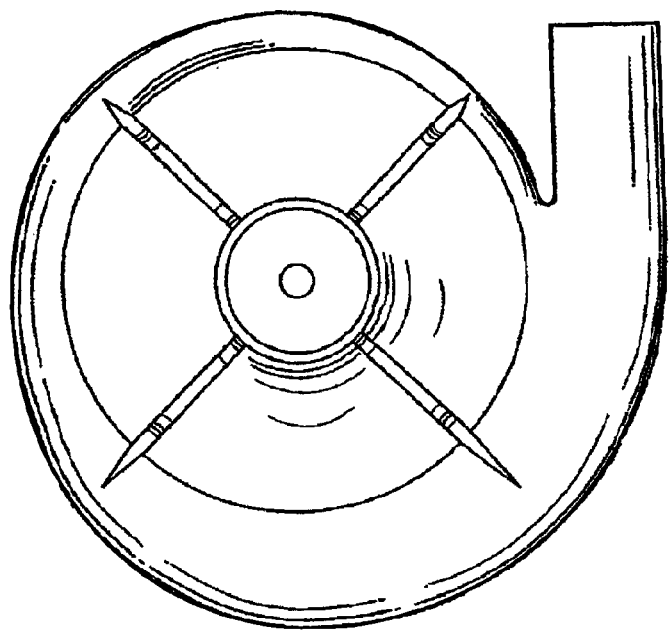
FIG. 3 shows a plan view of an example of a blower unit.
Figure 4:
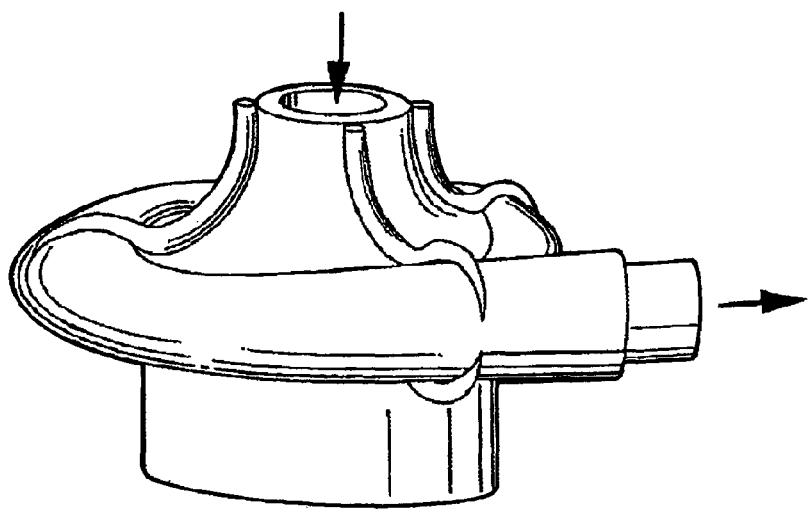
FIG. 4 shows a side view of the blower unit of FIG. 3.
Figure 5:
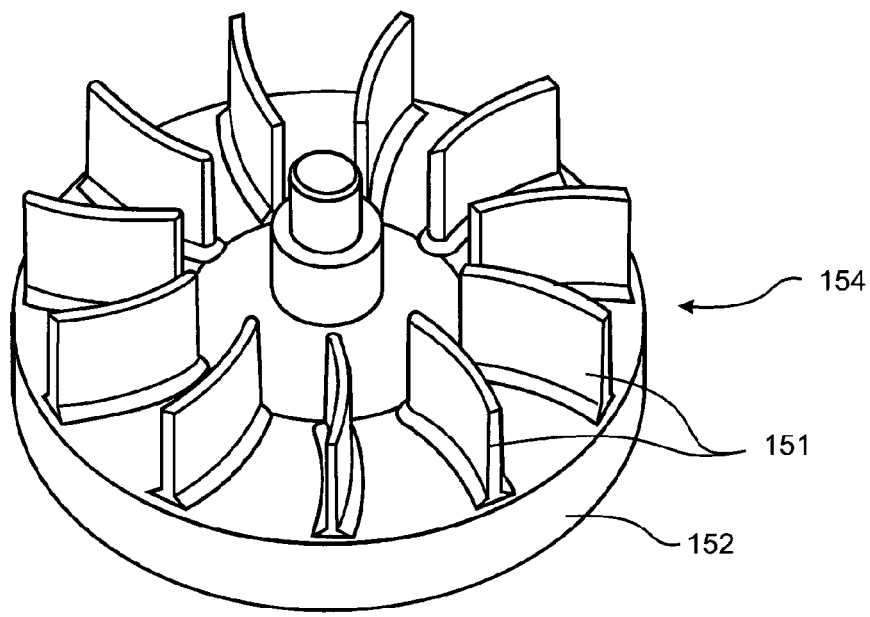
FIG. 5 shows a profile view of an impeller.
Figure 6:
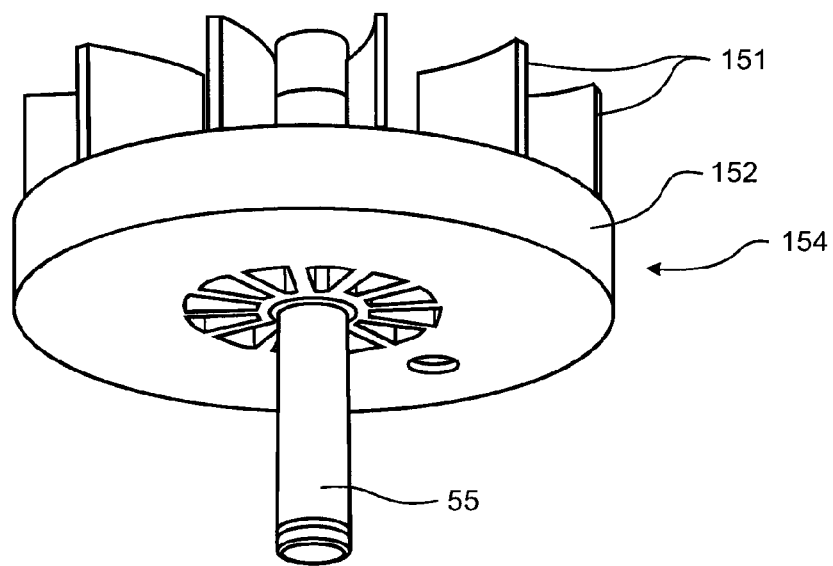
FIG. 6 shows another profile view of an impeller.

The preferred form of the impeller is shown in FIGS. 14 and 15. The impeller 24 has a plurality of blades 31 extending outward from a central hub 32. The impeller is a centrifugal impeller. The hub 32 defines the axis about which the impeller rotates. Preferably the hub 32 has an aperture or recess on the underside to allow engagement with a motor shaft which facilitates impeller rotation. However, other engagement mechanisms, such as over moulding of the hub with a shaft, could be used. When the impeller is rotated, air enters the impeller blades in the region proximate the hub 32, travels radially outward and exits the blades proximate the blade tips 33. The impeller is preferably made in one piece ("one piece construction"), as opposed to moulded in multiple parts and joined. This is possible when there is no shroud—or at most one shroud. This reduces misalignment of components that might lead to imbalance or other disadvantages. In the preferred embodiment there is no shroud (in contrast with for example the shroud 152 shown in FIGS. 5 and 6.)

The blades 31 preferably provide a substantially flat surface, from the hub 32 to the blade tip, and incident the direction of rotation to thereby centrifuge gases. Preferably the tips of the impeller blade tips 33 partially curve in the direction of impeller rotation ("arrow "A"). That is, the blade tips 33 are forward swept. Forward swept blade tips help to impart stronger rotational forces on the gases flowing through the impeller than straight or backswept blades. The forward swept blade tips help to produce a high pressure annulus between beyond tip of each blade. The inner portion 31 of the impeller blade may be somewhat backswept. A backswept blade allows for some recirculation of gases on the blade surface itself. The backswept inner blade portion may be beneficial to increase pressure generation and allow for stable low and reverse gases flow.

Figure 14A:
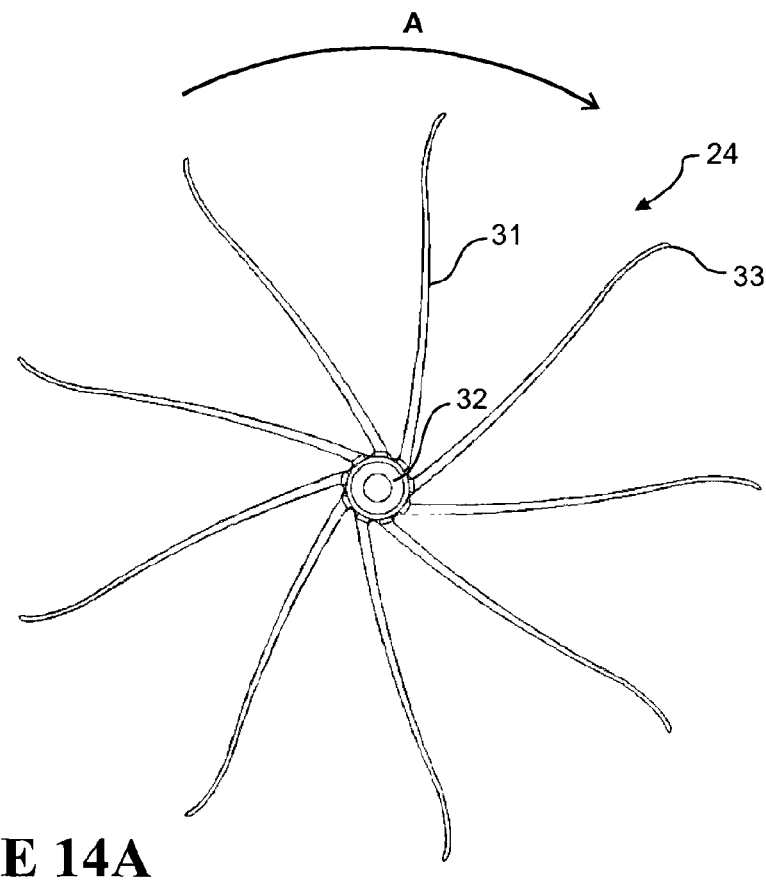
FIG. 14A shows a plan view of the impeller with no shroud according to one embodiment.
Figure 15A:
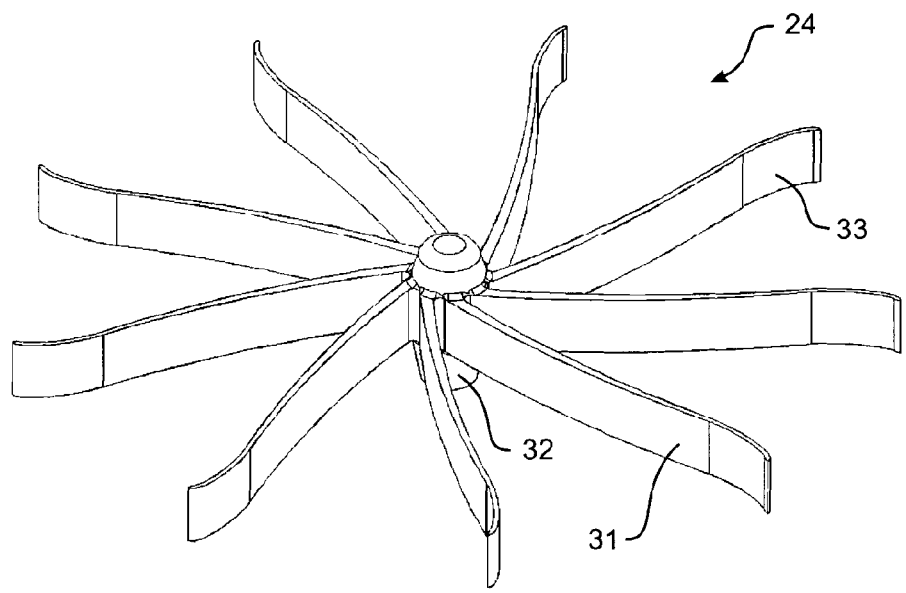
FIG. 15A shows a profile view of the impeller of FIG. 14a with no shroud.
Figure 14B:
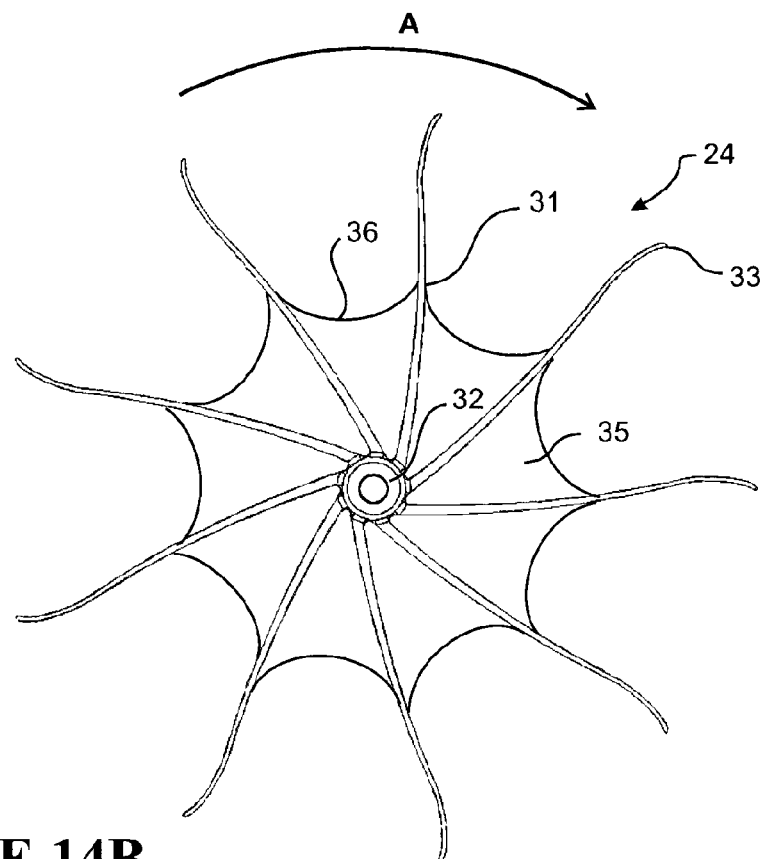
FIG. 14B shows a plan view of the impeller with reduced shroud material according to one embodiment.
Figure 15B:
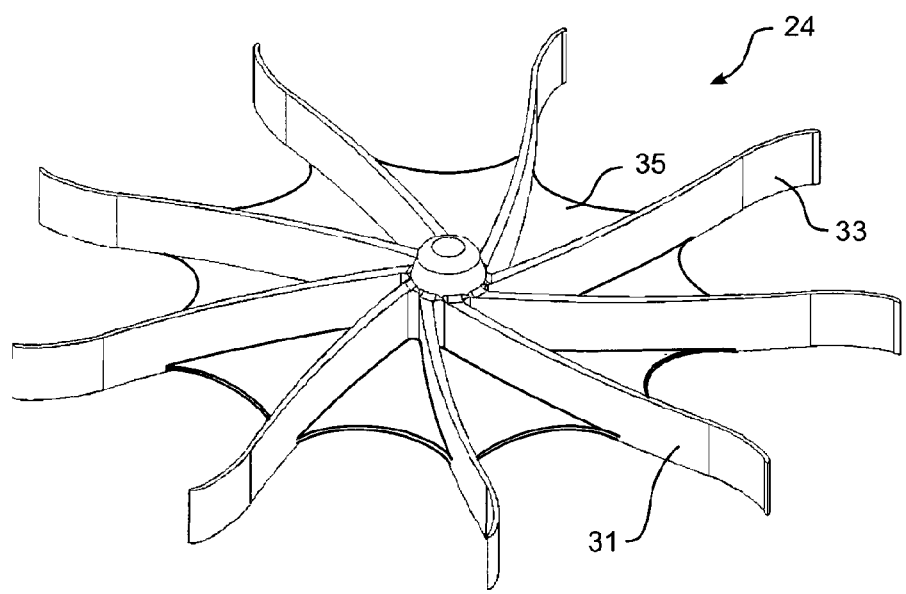
FIG. 15B shows a profile view of the impeller of FIG. 14*b* with reduced shroud material.
Figure 14C:
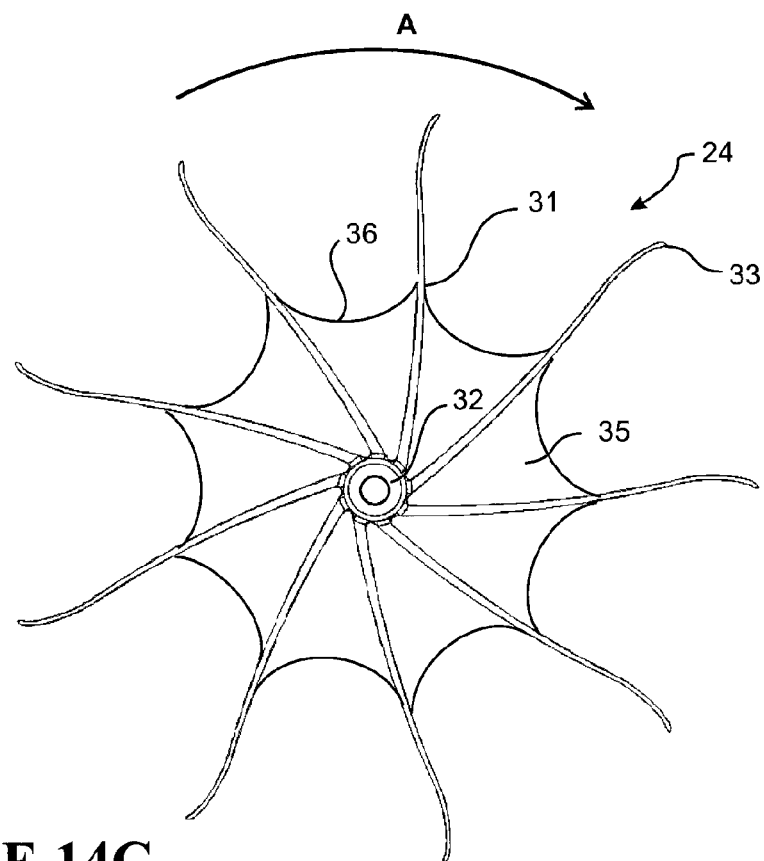
FIG. 14C shows a plan view of the impeller with a web structure.
Figure 15C:
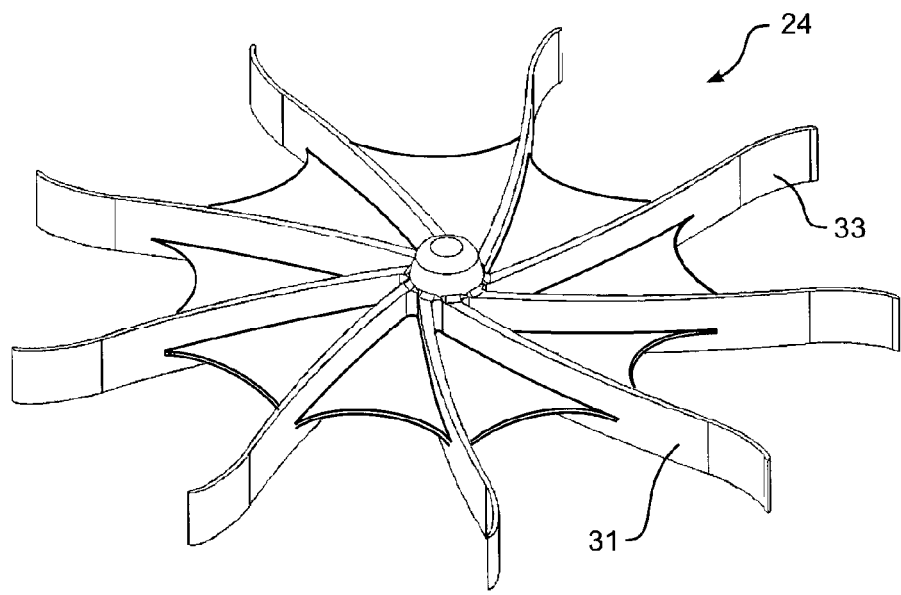
FIG. 15C shows a profile view of the impeller of FIG. 14*c* with a web structure.

The impeller is constructed to be lightweight. Preferably, this is by making the impeller shroudless, or at least partially shroudless, thereby removing weight. To achieve a lightweight impeller, as shown in FIGS. 14a and 15a, each of the blades 31 of the preferred impeller 24 are open between the blades (that is, the upper and lower "faces" or "planes" of the impeller are open to the internal surfaces of the housing of the fan unit 20) thereby defining a shroudless centrifugal impeller. By omitting a shroud on both the upper and/or lower faces of the impeller blades, the weight of the impeller 24 can be substantially reduced. The weight of the impeller can also be reduced in other ways, in addition to or alternatively to omitting the shroud. For example, a lightweight material can be used. Also, thin blades with minimal material and large gaps between blades could be implemented to reduce weight. Alternatively, a shroud 35 with some of the material removed, such as shown in FIGS. 14b, 15b could be used. A scalloped shaped 36 shroud is provided whereby some of the material between blades 31 is removed. Any suitable amount of material could be removed. A shroud channels air from the impellers. Where significant material is removed, the resulting structure may in fact no longer carry out this function of a shroud but rather just provide support for impeller blades 31. In this case, the impeller 24 may still be considered shroudless, despite having some structure between impeller blades 31. In yet a further embodiment shown in FIGS. 14c, 15c the structure between the impeller blades is a webbing that is disposed centrally between impellers. Such as structure does not function as a shroud. The reduced material structure or webbing 36 can be of any shape (not just scalloped) or extent, of which FIGS. 14b, 15b, 14c, 15c show two examples. A lightweight impeller 24 provides benefits such as manufacturing cost, low rotational inertia and is balanced or requires little effort to rotationally balance once manufactured. An impeller with low rotational inertia can be quickly accelerated and decelerated. A lightweight, shroudless impeller is therefore suited for quickly responding to fluctuating pressure requirements, such as the normal inhalation and exhalation cycle of a patient connected to the breathing assistance device in which the impeller operates.

Figure 29A:
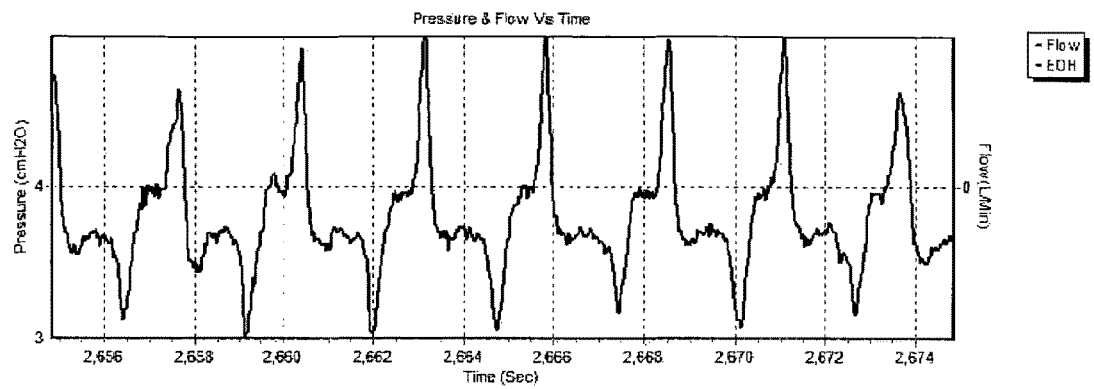
FIG. 29A is a pressure response graph of an earlier blower unit.
Figure 29B:
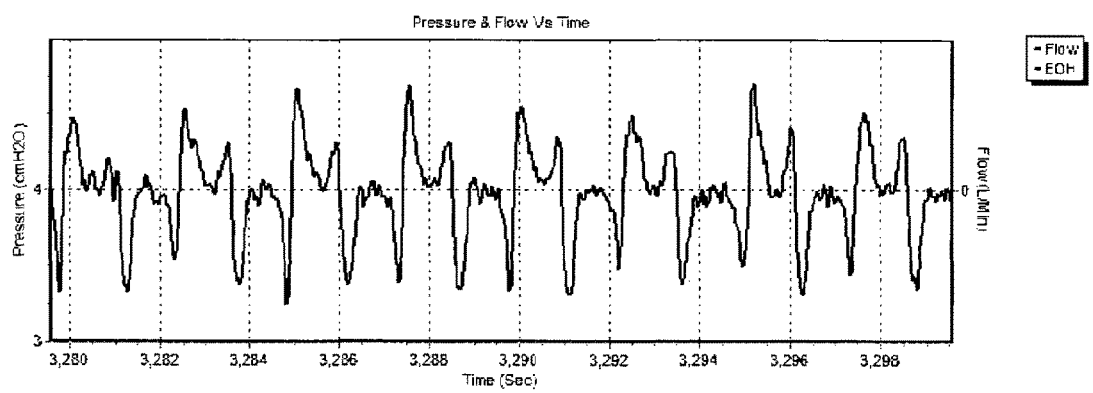
FIG. 29B is a pressure response graph of the blower unit of the present invention.

For example, a conventional shrouded impeller commonly used on a breathing assistance device, weighing approximately 17 grams and having inertia of 6 kg·mm2, can respond to pressure fluctuations of 10 cmH2O in approximately 2 seconds. By contrast, the preferred impeller, weighing approximately 1.7 grams and inertia of 0.5 kg·mm2, responds pressure fluctuations of 10 cmH2O in approximately 100 ms. FIG. 29A shows a graph of pressure verses time for the earlier impeller weighing 17 grams. The impeller is operated to attempt to maintain a constant pressure of 4 cmH2O during the normal inhalation and exhalation cycle of a patient. In comparison, FIG. 29B shows a graph of pressure verses time for the preferred impeller 24. It can be seen that the decrease in mass and rotational inertia over the earlier impeller exhibits much less pressure fluctuation that the impeller of FIG. 29A. The reduced pressure fluctuation is less disruptive to a patient's breathing process, and therefore advantageously increases patient comfort.

As mentioned, the lightweight can be achieved by omitting a shroud. However, it is not necessary to omit the entire shroud—rather just sufficient shroud to bring the weight of the impeller to a suitable level—such as shown in FIGS. 14B, 15B, 14C, 15C. Therefore, lightweight can be achieved by having as much open space (area or volume) between the blades as possible. The open space can be defined in terms of the blade volume to blade sweep volume ratio/percentage. That is, the blades sweep a volume X when rotating and the blades themselves have a combined volume Y (which is the volume of each blade combined). Alternatively, from a plan perspective, the open space can be defined in terms of the blade area to the blade sweep area. The ratios should be kept as low as possible. In one embodiment, for example the swept volume of the impeller is approximately 19,000 mm3, where the blades constitute a volume of approximately 1,200 mm3. The ratio of swept volume to blade volume is therefore approximately 16:1, thereby defining an impeller that is lightweight compared to the smaller, more densely designed and heavier impellers used earlier.

The lightweight impeller can have a weight for example of less than 2 grams and preferably between 0.8 and 1.8 grams, or more preferably, between 1.2 and 1.7 grams, or even more preferably 1.7 grams. These are just examples or a preferred embodiment and the impeller need not be this weight, but some other weight that renders it lightweight.

Alternatively, a lightweight impeller can be designed to remove as much of the shroud as necessary to bring the moment of inertia to radius ratio down to preferably less than 15 gram*mm, and more preferably between 8-12 gram*mm and in one possible embodiment approximately 11 gram*mm. For example, in one possible embodiment, such an impeller can have a radius of 35 mm, a circumference of 219 mm, and at 15,000 rpm a moment of inertia of 344.22, a tip speed of 54.98 m/s, a pressure of 1,800 Pa and a tip speed to inertia to radius ratio of 3.5 or more and for example 5.59. More generally, a lightweight impeller could have dimensions/parameters within the following ranges (note these ranges are indicative—not limiting):

Radius: 15 mm-60 mm

Weight: less than 2 grams

A pressure ratio to inertia to radius ratio of greater than 50:1 Pascals per gram*mm and preferably 80:1 Pa per gram*mm or more at 1,000 Pa.

Lightweight impellers enable larger radius impellers to be used. Yet larger radius impellers can be used than those mentioned above. Larger radius impellers provide greater tip speed and pressure. The construction of the impeller allows for greater radius impellers because the lightweight nature of the impeller is such that even with larger impellers, the inertia is still low enough to provide the required response and pressures.

The lightweight nature of the impeller can be achieved through removing mass through any suitable means, such as removing the shroud and/or material from the impeller and/or using lighter materials. One possible manner in which to reduce impeller mass is to reduce the number of blades.

The impeller generates a high pressure annulus between the tip and inner face of the housing. The backward facing impeller with a forward sweep at the tip also allows for recirculation on the blade itself, which helps with increased pressure generation and stable flow and reverse flows.

Figure 16:
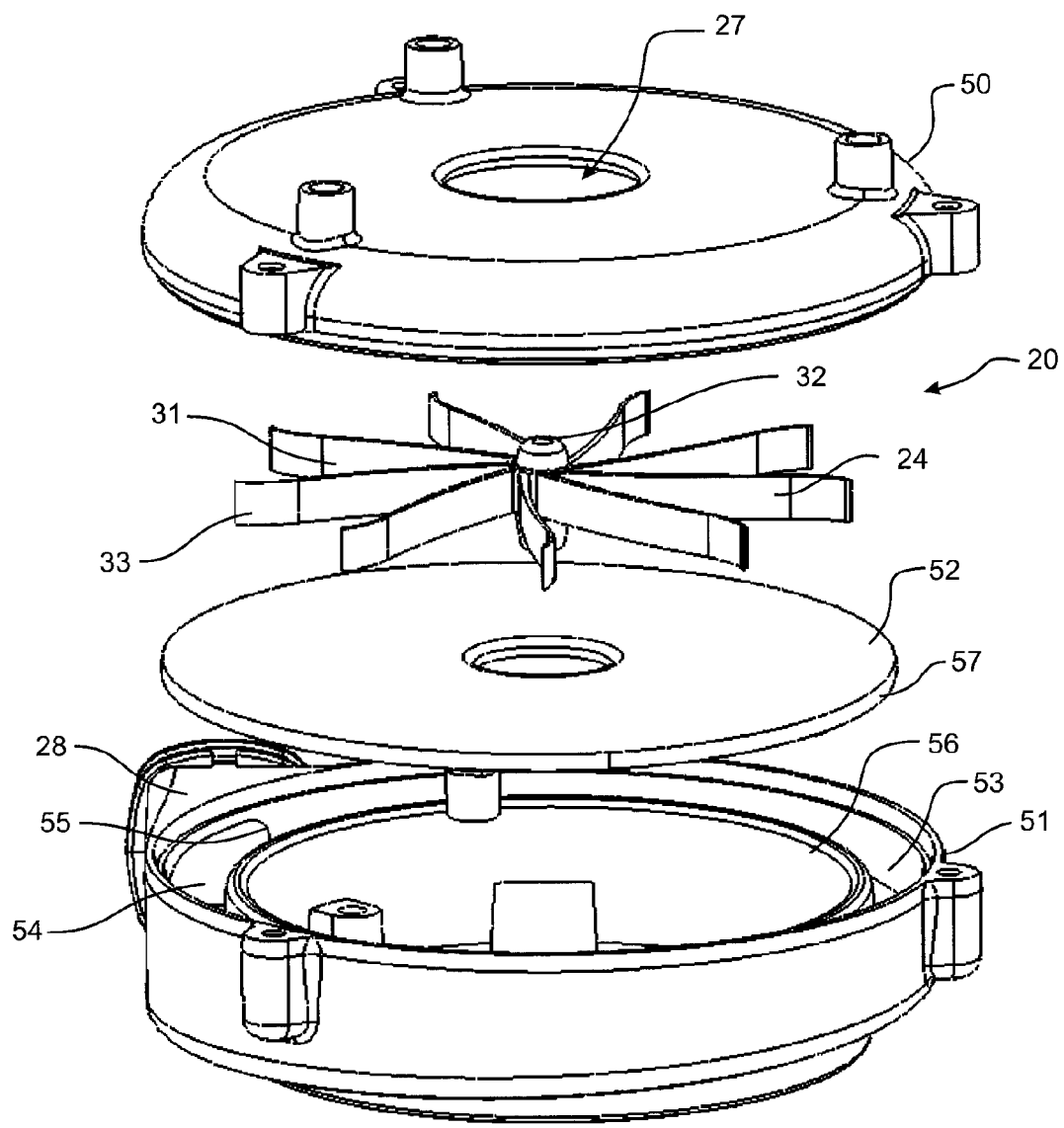
FIG. 16 shows an exploded view of the preferred housings and impeller of one embodiment.

The fan unit 20 as shown in FIGS. 11 and 12 and described above is shown in exploded form in FIG. 16. The blower has an upper housing layer 50 and a lower housing layer 51 that assemble to encapsulate a partitioning layer 52 and the impeller 24. The blades of the impeller are open to the internal surfaces of the upper and lower housing layers. The partition layer 52 and the inner surface of the upper layer 50 are profiled to substantially enclose the impeller blades when the layers are assembled. This forms a first interior region ("upper region"). The upper housing layer 50 has the aperture 27 that defines the gases entry into the blower. The lower housing layer defines a volute 53 where gases are collected before emission from the blower. Preferably the volute 53 also has a sealing inner wall 56. The wall 56 defines a space internal to the lower housing that may be used to house a motor. The lower housing layer 51 and the partition 52 form a second interior region ("lower region").

The outlet passage 28 of the fan unit 20 is connected to the volute 53 via an aperture 54. The aperture 54 and the volute wall 53 define a tongue 55 whereby gases circulating in the volute 53 are diverged into the outlet passage 28.

The partition layer 52 is generally circular and substantially divides the upper housing 50 from the lower housing 51 thereby defining the upper and lower gases flow (interior) regions of the blower. To allow gases to flow from the upper region to the lower region an aperture (opening) 57 is located at, or close to the outer edge of the partition. The aperture 57 is shown more clearly in FIGS. 17 and 18. The aperture 57 is most preferably an opening formed by a cut-away in the partition layer 52, or some other configuration/shape of the housing 51 such that the combination/arrangement of the partition layer 52 and the housing 51 creates an aperture/opening between the two. However, the aperture 57 may also comprise a flow path formed separately to the partition layer, such as a bulge or fluid channel formed in the walls of the upper 50 and lower housings 51. The cut-away could form a circumferential aperture 57 between the housing 51 and partition 52, for example. The curvature/centre of radius of the circumferential aperture 57 is preferable offset from the centre of radius of the partition 52 or otherwise has a curvature that differs from that of the circumference of the partition 52 resulting in an eccentric or otherwise offset circumferential aperture 57 around the circumference of the partition 52 as shown in the Figures. This produces an aperture 57 with a crescent ("smile") shaped opening that spans a leading edge 58 to a trailing edge 59. However, the aperture may be of any shape with a gradual opening and closing relative to the plane of impeller rotation. The aperture allows for gradual supply of pressure and flow from the high static pressure source at the top of the blower. The angle of the aperture opening and closing is tuned to allow for reverse flow to return through the system in a stable fashion. It also contributes to the blade pass noise reduction by not having a sharp break in geometry. The aperture provides addition tongues, as well as that on the outlet. The gradual opening and closing of the aperture ("tapers") provides tongues. The maximum velocity at the outlet (e.g. 10 m/s) is less than that at the tapers (e.g. 60 m/s). The gradual opening and closing with blades passing at that speed manages blade pass noise. The width and length of the aperture 57 controls the velocity in the lower (volute) section of the housing. A wider and longer aperture increases velocity in the volute, for example.

Figure 17:
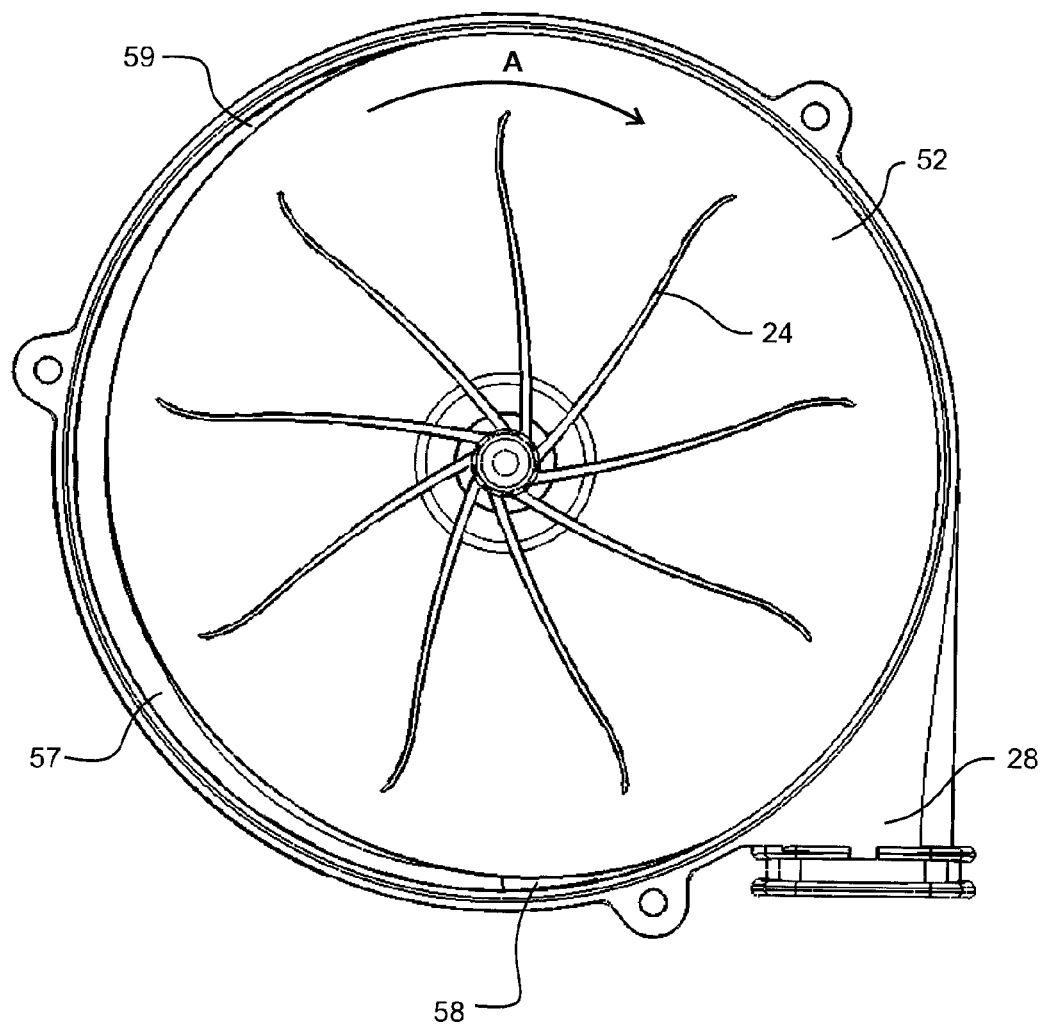
FIG. 17 shows a plan view of the lower housing, partition and impeller of one embodiment.
Figure 18:
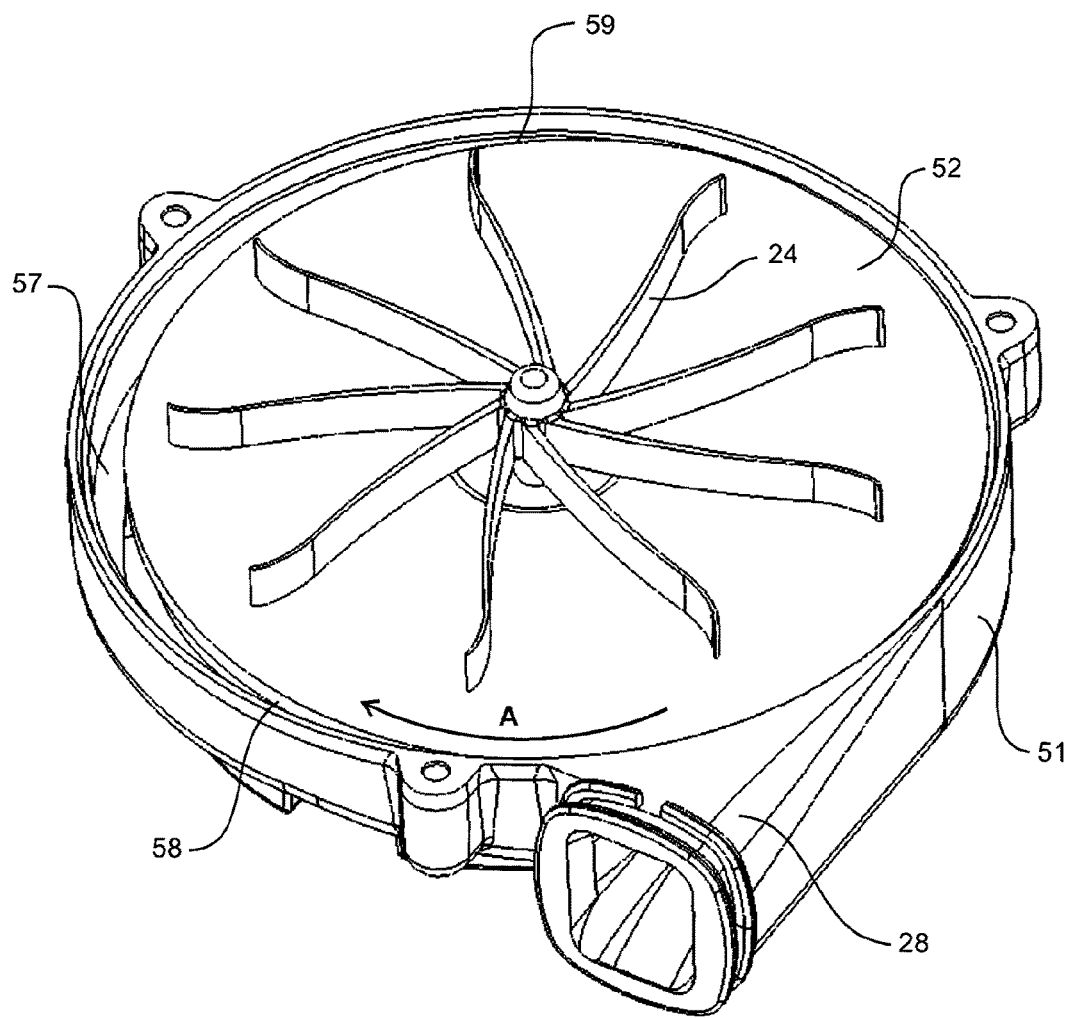
FIG. 18 shows a profile view of the components of FIG. 17.

During operation of the blower, the impeller 24 is rotated in direction A—see FIG. 17. The rotation of the impeller 24 draws gases through the inlet 27 and through the blades 31 toward the outer wall of the upper housing layer 50. During operation, air B can also be drawn through the stator/rotor from the other side of the housing—see e.g. FIG. 13. The air B drawn through can cool the motor. The shroudless impeller 24 enables air to be drawn through the motor in this manner thus providing cooling. The forward swept blade tips 31 impart strong rotational forces to the gases circulating in the upper region of the blower housing to thereby create high circulating gas speeds. Gases in the upper region will naturally flow through the aperture 57 to the lower region due to pressure differential between regions. When the gases in the upper region, having a high velocity and low pressure, enter the lower region, specifically the volute 53, the gas velocity drops and the pressure increases. Typically the volute 53 has a greater volume than the upper region to help facilitate a gases pressure increase.

By dividing the blower internal space into two separate regions a number of advantages can be realised. In a conventional blower, high velocity gases leaving the impeller are incident to the edge, or tongue, that defines a physical boundary where gases are split from the volute to enter the outlet passage. High velocity gas flow at incident the tongue is turbulent and inefficient to blower performance. The turbulence caused by the tongue also introduces a source of noise. In contrast, dividing the housing of the preferred blower into the upper and lower regions reduces the impact caused by the tongue. The upper region allows the gases to circulate at a high speed. The gradual radial opening and closing of the preferred partition 57 provides a fluid path to the lower region that is free from (or has reduced) aerodynamically turbulent edges. When circulating gases have entered the lower region, the enlarged volume of the volute encourages the gases to slow and increase pressure. The reduced gases velocity reduces the impact of turbulence normally caused by the tongue 55 to a low or negligible level. The blower unit is therefore able to operate across a wide pressure and flow range with substantially reduced noise output when compared to other blowers. A wider and longer aperture 57 increases the flow rate of the lower region relative to the upper region. Therefore, the size of the aperture is selected according to the desired flow rate and pressure range of the blower unit.

Figure 19:
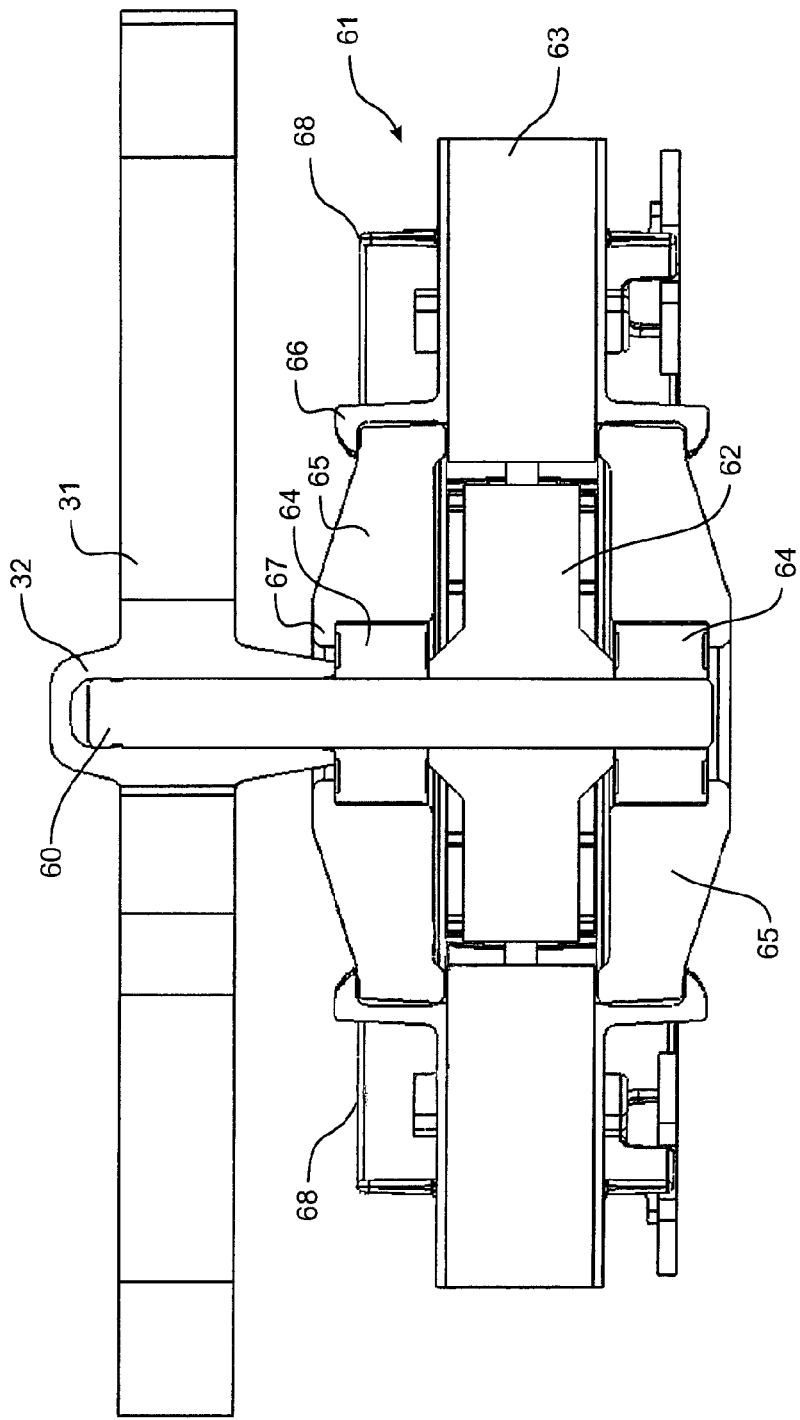
FIG. 19 shows a cross sectional view of the motor and impeller of one embodiment.

The motor used to drive the impeller 24 is shown in cross section in FIG. 19. Preferably the motor is a brushless DC motor operated using sensorless vector control (also termed "field oriented control") controlled by a microcontroller, microprocessor or similar controller 14 (such as shown in FIG. 7), for example, via the connector 131 mounted to a PCB 130. The control can be tuned to suit a low inertia impeller. The central hub 32 of the impeller 31 is engaged with a shaft 60 that extends from the motor 61. Mounted to the shaft is a plurality of, preferably small, magnetic segments to form a rotor 62. In one embodiment the magnet is 20 mm in diameter, but more generally the diameter could be less than 20 mm and preferably between 10 mm to 15 mm. The magnet volume is less than 1600 mm3 and can be between 500 mm3 and 1600 mm3. Surrounding the rotor 62 is a laminated stator having a plurality of poles 63 and windings 68. The stator is mounted to the PCB or other substrate 130 and the windings coupled to the connector 131. The windings are selectively energised by the microcontroller 14 via the connector 131 to facilitate rotation of the rotor, and therefore the shaft 60 and impeller 31, about the central axis defined by the centreline of the shaft 60.

The shaft 60 is held within the motor by a bearing structure. Preferably the bearing structure has one or more bearings 64 and one or more bearing mounts 65. The bearing mounts 65 as shown engage with the bearings on an inner surface and with the stator on an outer surface. The preferred engagement of the mount to the bearings and the stator is frictional. To promote a frictional engagement, the bearing mounts 65 are made of a soft, yet resilient and/or flexible material such as silicone rubber or other elastomeric material. The material can be low creep, temperature stable, low compression set with a high tan delta (highly viscous), highly damped. Examples comprise:

Dough Moulding Rubbers like—NBR, Nitrile and Flouro silicone.

Thermo Plastic Elastomers (TPE's) like Santoprene by Exxon

Thermo Plastic Urethanes like Dynaplast by GLS Corporation

Heat Cured Casting Urethanes like 10T90 by National Urethanes

Multiple other cold cast rubbery compounds like RTV (Room Temperature curing Vulcanites) by Dow Corning, Whacker and others.

Such materials allow the mounts 65 to compress when installed, then expand into their chosen location to be held in place by engagement expanded dimension with a restriction. The mounts 65 are optionally restrained by an overhang 66 formed as part of an electrical insulator/isolator or other frame structure ("stator frame") on the stator. Similarly, the bearings may be restrained by an overhang 67 formed as part of the bearing mount. Either or both of the overhangs may be discretely positioned about the inner and outer annulus of the bearing mounts, or alternatively, extends around the circumference of the mount to define a recess in which the mount is located.

The bearing mounts provide compliance to the rotatable shaft 60. As rotatable objects, such as the rotor 62, shaft 60 and impeller 31 usually suffer from some degree of rotational imbalance, the bearing mounts are able to isolate inherent rotation induced vibration from the motor rotor. It has been found that combination of the lightweight, shroudless impeller having a low rotational inertia, as described above, together with the given compliance of the bearing mounts enables the rotor 62, shaft 60 and impeller 31 to be manufactured and any post manufacture balancing process for the rotating components entirely omitted. These advantages benefit manufacturing costs and time. The lightweight nature of the impeller allows any imbalances to be compensated by the bearing mounts. A lightweight impeller also allows faster speed response of the impeller to changing conditions. Any unwanted fluctuations in pressure due the lack of shroud can be compensated for by quickly changing the impeller speed to return pressure to the desired level.

It should be noted that while FIG. 19 shows the bearing mounts 65 mounted within the motor stator, they may equally be housed externally to the motor. For example, the mounts 65 may instead be mounted within journals formed within the blower housings, or the gases supply unit 7. In such circumstances where the bearing mounts are located within the gases supply unit 7, it may also be advantageous to omit discrete structures for the blower housing 50, 51, instead mounding the inner surfaces of the housings directly to the internal structure of the gases supply unit 7.

Figure 20:
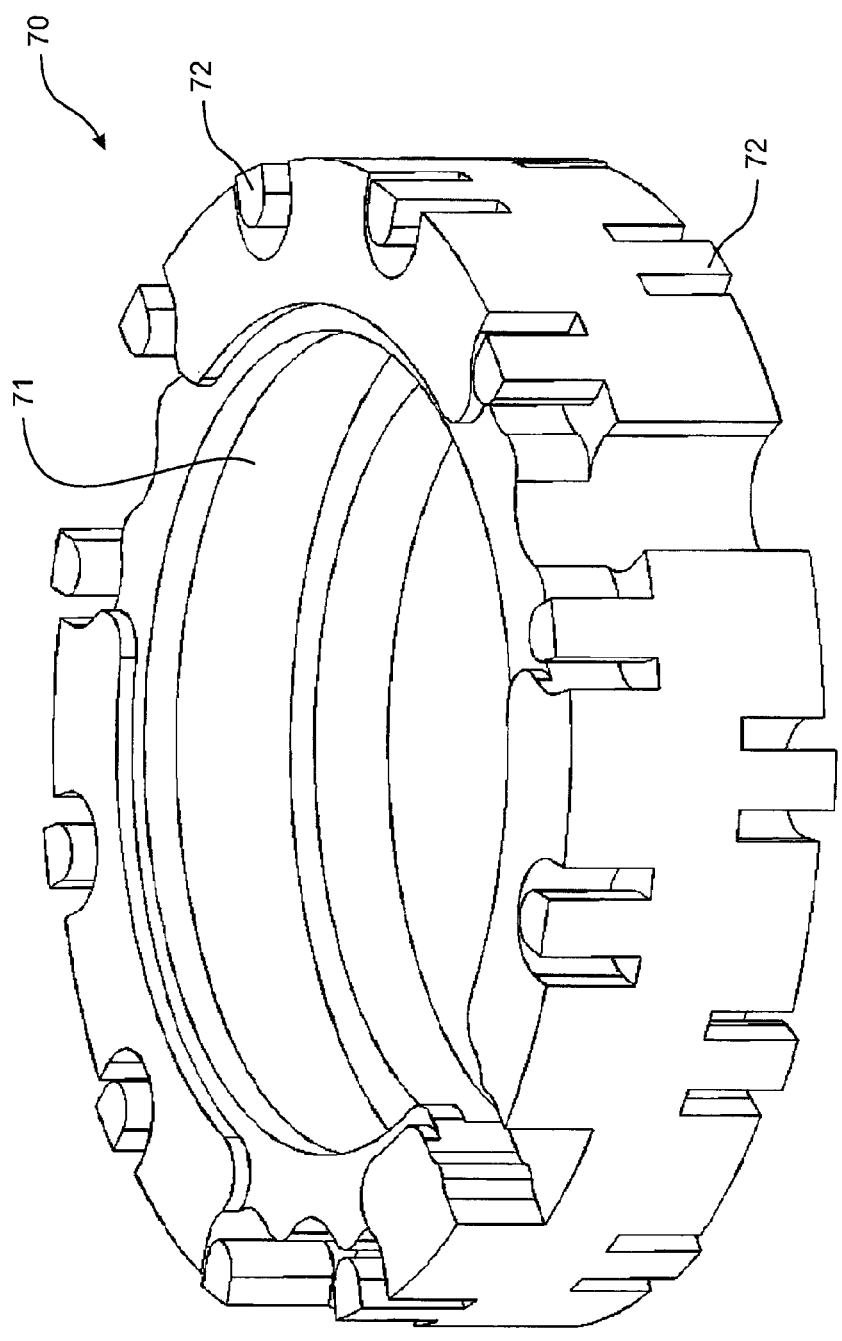
FIG. 20 shows a motor mounting structure one embodiment.
Figure 21:
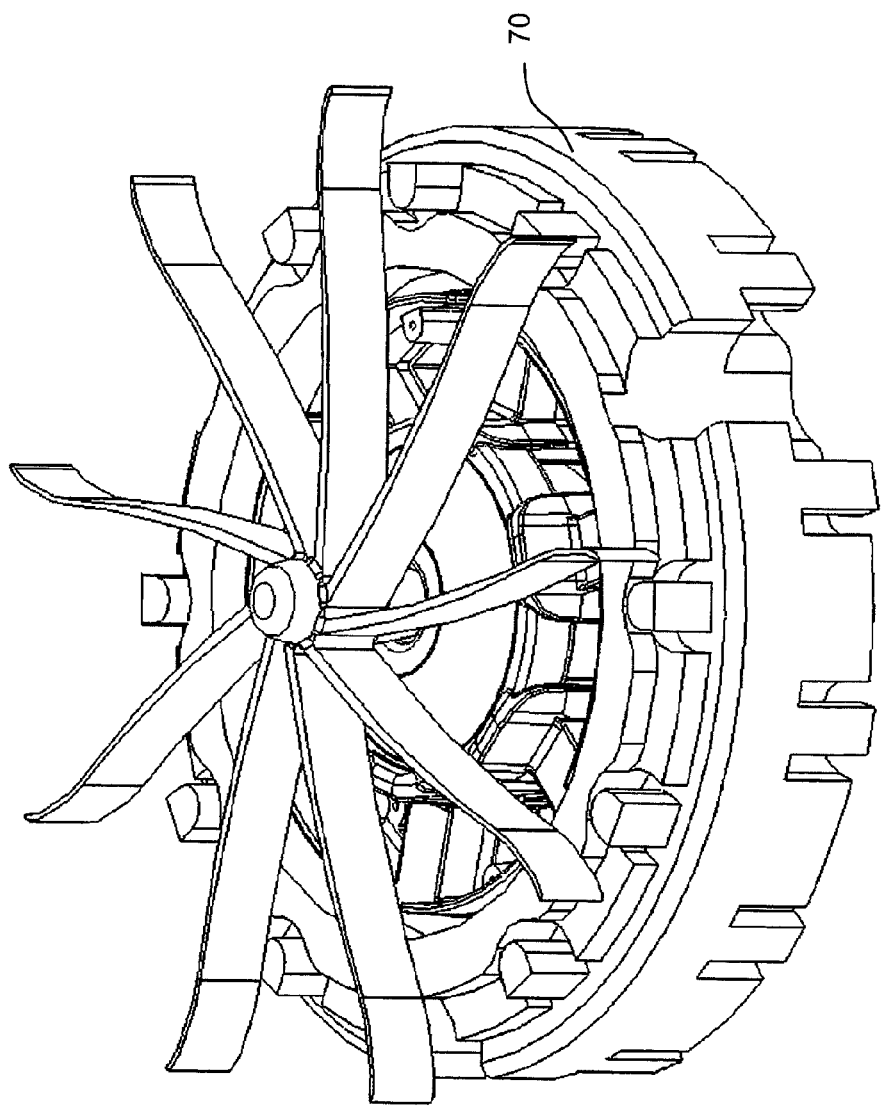
FIG. 21 shows the motor mounting structure with a motor and impeller of one embodiment.

To provide further vibration damping of the rotational components of the blower, the motor and impeller, can optionally be mounted on a compliant mounting device. FIG. 20 shows one embodiment of such a mounting device 70. In accordance with the preferred embodiment of the invention the mount is most preferably made from a soft, flexible yet resilient material such as silicone rubber. The mounting device 70 has an internal recess 71 in which the stator is relieved. Preferably the internal recess is smaller than the outer surface of the motor to encourage an interference fit between these components. FIG. 21 shows the motor 61 positioned within the mounting recess 71.

A plurality of projections 72 encircles the upper and lower surfaces of the mount 70. Each projection 72 preferably has a base recessed into the body of the mount to effectively increase the length whereby the projections are free to bend. The end of projection extends past the upper and lower surfaces of the mount to provide supporting leverage to the mount and motor assembly. During operation of the motor, vibration caused by any imbalance of the rotational components is absorbed by each of the projections by allowing the body of the mount 70 to move relative to the surface on which the projections 72 are supported.

Figure 22B:
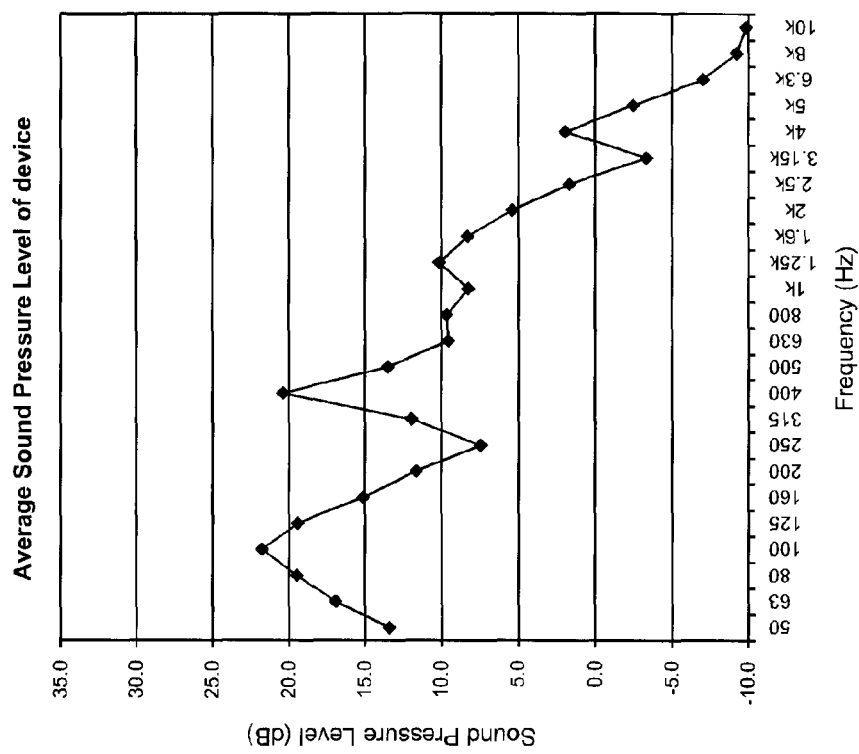
FIG. 22B is a graph of average sound pressure levels of the blower unit of the present invention.
Figure 22A:
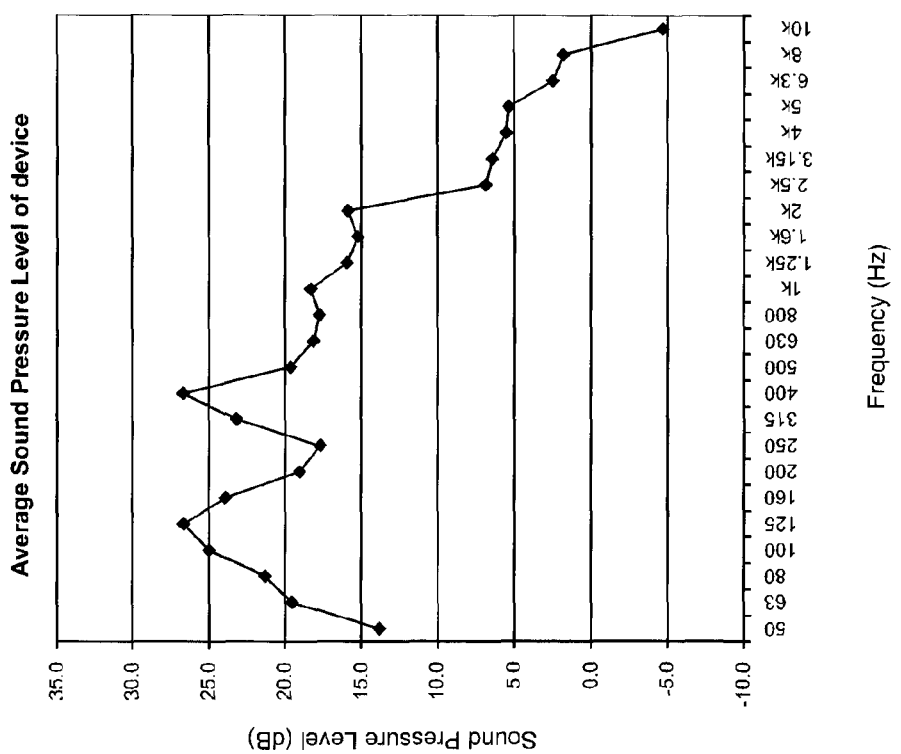
FIG. 22A is a graph of average sound pressure levels of an earlier blower unit.

FIG. 22A is a graph of the sound pressure level of a conventional fan unit tested in an anechoic chamber. FIG. 22B is a graph of the sound pressure lever of a fan unit according to the present invention. It can be seen that the lightweight and shroudless impeller 24, the flexible bearing mounts 65 and flexible motor mount 70 contribute to a significantly reduced noise output across the tested spectral range of 50 Hz to 10 kHz.

Figure 23:
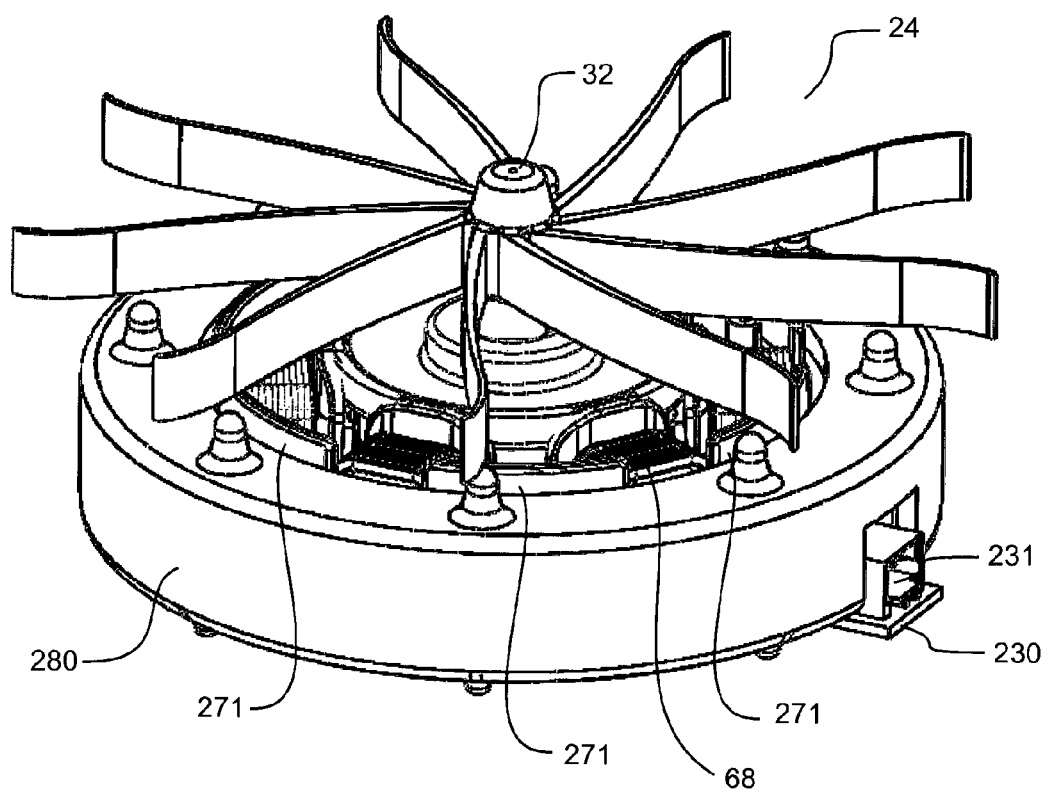
FIG. 23 shows the motor mounting structure with a motor and impeller of a second embodiment.
Figure 24:
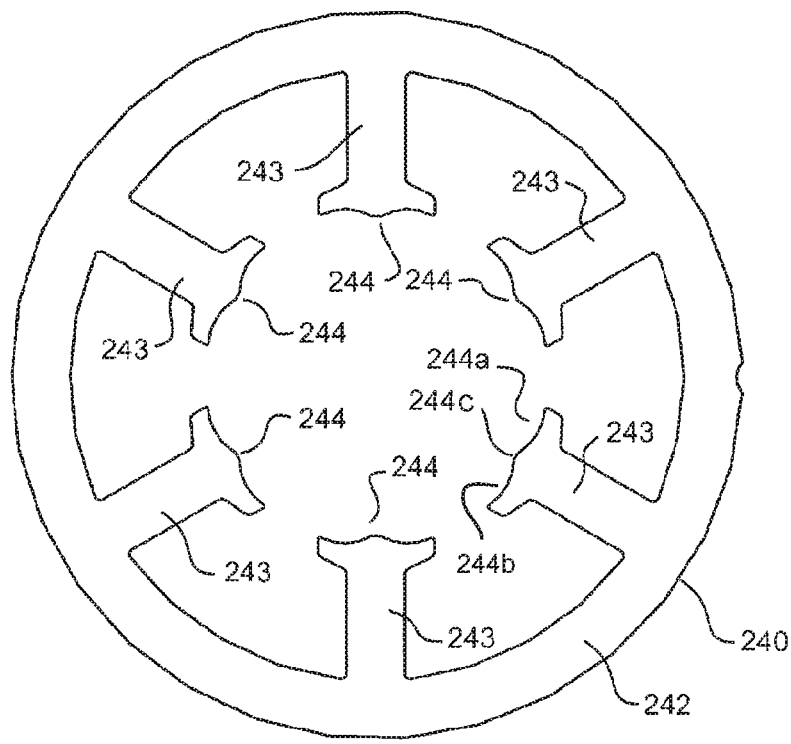
FIG. 24 shows a stator lamination of the second embodiment.
Figure 27:
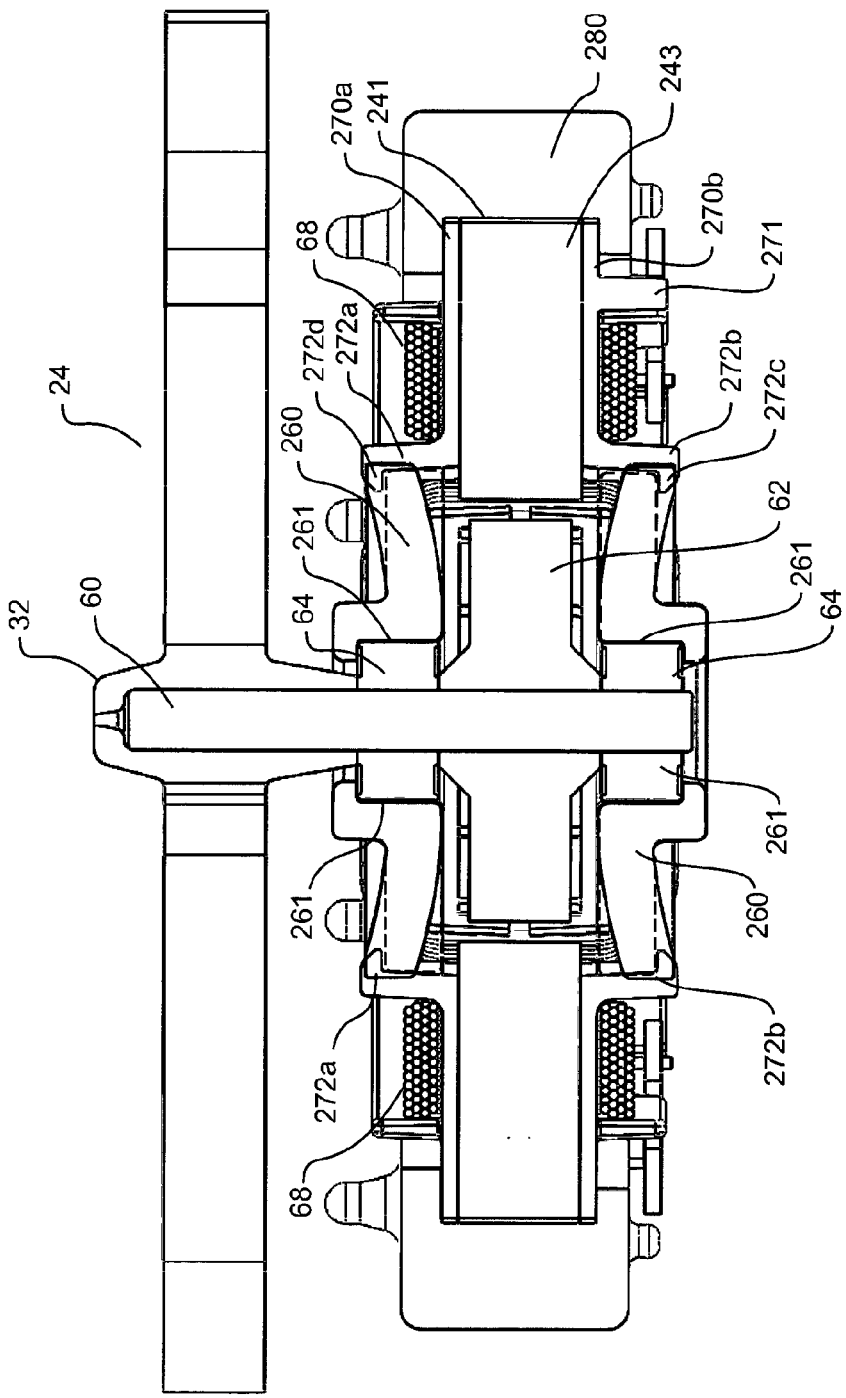
FIG. 27 shows a cross sectional view of the motor and impeller of the second embodiment.

A further embodiment of the motor and impeller assembly is shown in FIGS. 23 to 28. Many aspects of this embodiment are the same as those in the previous embodiment. Features described in relation to the previous embodiment not described in this embodiment can be assumed to exist in this embodiment where appropriate. Like features will use the same reference numerals as the previous embodiment. The motor used to drive the impeller 24 is shown in cross-section in FIG. 27. Preferably the motor is a brushless DC motor operated using sensorless vector control ("field oriented control") controlled by a microcontroller, microprocessor or similar controller 14 (such as shown in FIG. 7), for example, via a connector 231 mounted to a PCB/substrate 230 (such as shown in FIG. 23). The control can be tuned to suit a low inertia impeller. Referring to FIGS. 23, 24 and 27, the central hub 32 of the impeller 24 is engaged with a shaft 60 that extends from the motor 61. Mounted to the shaft is a plurality of, preferably small, magnetic segments to form a rotor 62. Surrounding the rotor 62 is a laminated stator 241 having an annular outer portion 242 and a plurality of poles 243 and windings 68. The stator is mounted to the PCB or other substrate 230 and the windings 68 coupled to the connector 231. The stator 241 has an electrical insulator/isolator (forming a stator frame) 270a, 270b covering the top and bottom of the annular portion 242 and the poles 243. Each winding 68 is preferably assembled on the insulator 270a, 270b over each pole 243. Protrusions for engagement and retainment are provided around the circumference 271 extending upwards and at the end of the poles extending upwards 272a and downwards 272b.

Figure 25:
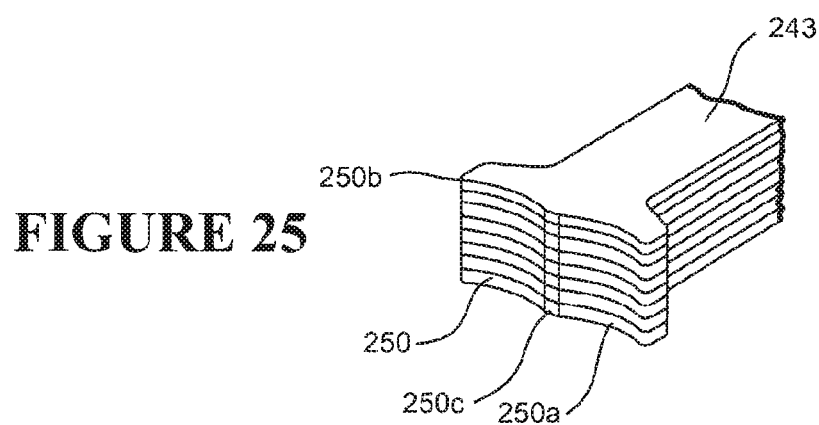
FIG. 25 shows a pole face of the second embodiment.
Figure 26:
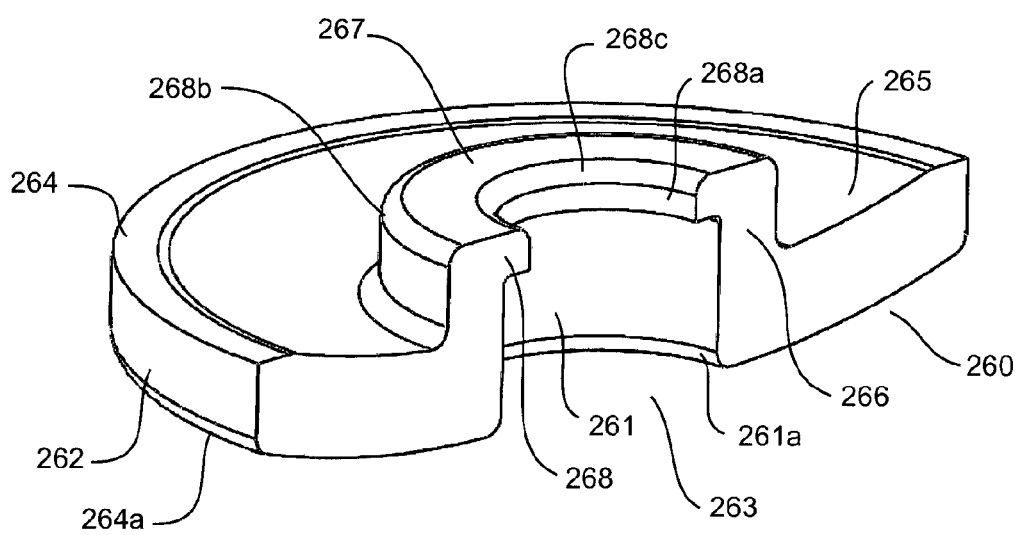
FIG. 26 shows a bearing mount of the second embodiment.

Referring to the plan view of one of the laminations 240 in FIG. 24, each lamination comprises a annular outer portion 242 and a pole portion 243 extending radially inwards. The edge 244 of each pole portion 243 includes a wave shape. The wave shape comprises two concave portions 244a, 244b meeting at a central apex 244c. Referring to FIG. 25, when a plurality of the laminations 240 are stacked to create the stator 241, each pole 243 has an inner radial face 250 with a wave shape as shown in FIG. 25. The face 250 comprises two concave portions 250a, 250b meeting at a central apex 250c. This arrangement reduces cogging. The stator and/or rotor can have a skewed magentisation. The windings are selectively energised using the controller 14 via the connector 231 to facilitate rotation of the rotor, and therefore the shaft 60 and impeller 31, about the central axis defined by the centreline of the shaft 60.

The shaft 60 is held within the motor by a bearing structure. Preferably the bearing structure has one or more bearings 64 and one or more bearing mounts 260 (see FIG. 26). The bearing mounts 260 as shown engage with the bearings 64 on an inner surface 261 and with the stator 241/insulator 270a/270b on an outer surface as shown in FIG. 27. The bearing mount 260 comprises a main annular body 265 that curves from a low point at a central aperture 263 to a higher point at the outer circumference 262. The outer circumference comprises an engaging lip 264, preferably with a chamfer 264a on the intersection of the outer circumference 262 with the main annular body 265. The intersection of the inner aperture 263 with the inner circumference 261 of the main body 265 also preferably has a chamfer 261a. An annular wall/boss 266 extends upwardly from the main annular body 265 at the inner aperture 263. The top portion 267 of the annular wall 266 has an overhanging engagement lip 268. The intersection of the lip 268 with the annular wall 266 and with the overhanging lip side wall 268a are preferably chamfered 268b, 268c. The preferred engagement of the bearing mount 260 to the bearings 64 and the stator 241 is frictional. To promote a frictional engagement, the bearing mounts 260 are made of a soft, yet resilient and/or flexible material such as silicone rubber or other elastomeric material. The material can be low creep, temperature stable, low compression set with a high tan delta (highly viscous), highly damped. Possible materials were describe in relation to the previous embodiment. Such materials allow the mounts 260 to compress when installed, then expand into their chosen location to be held in place by engagement expanded dimension with a restriction. They also provide compliance.

FIG. 27 shows the bearing mounts in solid lines in the uninstalled/unassembled state, with an upward curvature. The dotted lines show the bearing mounts 260 in the installed/assembled state, clipped in to the stator/insulator 270a, 270b. In the installed state (also called engaged state or configureation) the annular body is engaged with the stator 241 and/or stator frame 270a, 270b and the annular body 265 is coerced from the curved state (shown in solid lines) into an engaged (flat) configuration (shown in dotted lines) that provides preload to the one or more bearings by action of the bearing mount providing bias provided by the resilient/flexible body acting on the stator and/or stator frame and the bearings. The mounts 260 are optionally restrained by an overhang 272c, 272d formed on the insulator 270a, 270b. Similarly, the bearings 64 may be restrained by an overhang 268 formed as part of the boss 266 on the bearing mount 260. Either or both of the overhangs may be discretely positioned about the inner and outer annulus of the bearing mounts, or alternatively, extends around the circumference of the mount to define a recess in which the mount is located. The impeller/shaft/rotor is assembled into the stator 241 by assembling the bearings 64 on the shaft 60, assembling the bearing mounts 260 on the bearings 64 and manipulating the bearing mounts 260 (by hand, jig or other means) so they engage with the stator insulator 270a, 270b at each pole 243. In an alternative embodiment, the bearing mounts 260 are not coupled directly to the stator or insulator 270a/241 but rather are coupled to another structure such as a housing. Any coupling arrangement with any suitable structure can be provided which provides the required functions as set out below.

The bearing mounts 260 provide compliance to the rotatable shaft 60. As rotatable objects, such as the rotor 62, shaft 60 and impeller 24 usually suffer from some degree of rotational imbalance, the bearing mounts are able to isolate inherent rotation induced vibration from the motor rotor. It has been found that combination of the lightweight, shroudless impeller having a low rotational inertia, as described above, together with the given compliance of the bearing mounts enables the rotor 62, shaft 60 and impeller 24 to be manufactured and any post manufacture balancing process for the rotating components entirely omitted. These advantages benefit manufacturing costs and time. The lightweight nature of the impeller 24 allows any imbalances/misalignment to be compensated by the bearing mounts 260—the arrangement is self aligning due to the bearing mount compliance (due to resilience and/or flexibility, for example). The bearing mount construction, including the geometry and material, also provides axial preload on the bearings, e.g. of up to 7 Newtons. The annular nature of the bearing provides consistent/even preload around the bearing 64. The resilien/flexible curved annular body allows the bearing to be installed in place and provide the preload. The annular nature of the bearing mount 260 provides for even preload around the bearing, while the low creep construction material maintains preload. The material of the bearing mounts 260 is also preferably a viscoelastic damping material that provides damping, which reduces the likelihood of resonance during operation of the motor. Such a viscoelastic material can also provide the required resilience/flexibility to provide the preload. An example of such a material is a Thermo Plastic Urethane like Dynaplast by GLS Corporation. Other materials resilient and/or flexible materials mentioned above for the bearing mount 260 could be adapted to provide the required damping by adding mica. A lightweight impeller also allows faster speed response of the impeller to changing conditions. Any unwanted fluctuations in pressure due the lack of shroud can be compensated for by quickly changing the impeller speed to return pressure to the desired level. The bearing mounts also provide vibration isolation.

Figure 28:
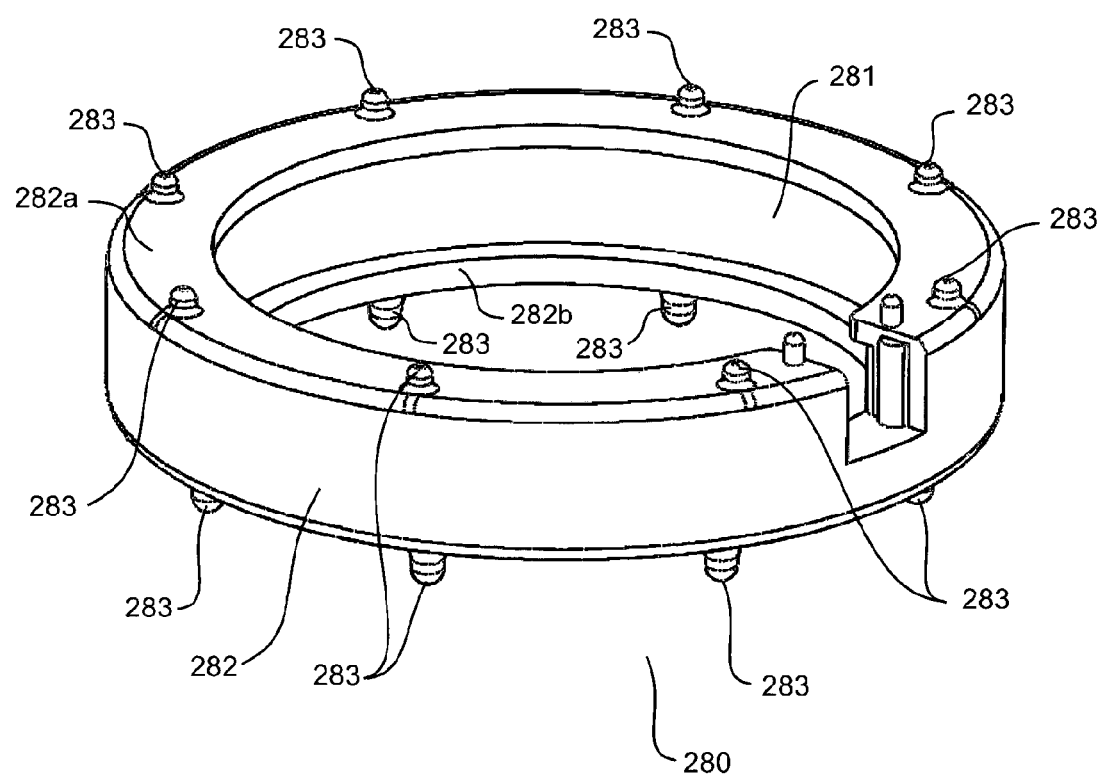
FIG. 28 shows a motor mounting structure of the second embodiment.

To provide further vibration damping of the rotational components of the blower, the motor and impeller, can optionally be mounted on a compliant mounting device (motor mount) 280. FIGS. 23, 27 and 28 shows one embodiment of such a mounting device 280. In accordance with the preferred embodiment of the invention the mount is most preferably made from a soft, flexible yet resilient material such as silicone rubber. The mounting device 280 has an annular body 282 with upper and lower engaging lips 282a, 282b that define an internal recess 281 in which the stator 241 is disposed. Preferably the internal recess 281 is smaller than the outer surface of the stator to encourage an interference fit between these components. FIG. 27 shows the motor positioned within the mounting recess 281.

A plurality of projections 283 encircles the upper and lower surfaces of the mount 280. The end of projection extends past the upper and lower surfaces of the mount to provide supporting leverage to the mount and motor assembly. During operation of the motor, vibration caused by any imbalance of the rotational components is absorbed by each of the projections by allowing the body of the mount 280 to move relative to the surface on which the projections 283 are supported.

The combination of various features of the present invention provide advantages, which can be achieved using a single impeller. Using a lightweight/low inertia impeller (e.g. by removing some or all of the shroud and/or reducing blade material) reduces imbalance of the impeller due to manufacturing tolerances. Previously, after manufacture and during assembly of a blower, it has been necessary to remove/add material to the impeller to improve balancing. The lightweight nature of the impeller means that any small imbalance can be tolerated without requiring rectification. Coupled to this, where the imbalance is not small enough, the resilient/flexible bearing structure mounts 65 and/or stator mount can compensate for any imbalance in the impeller. As the impeller is lightweight enough, any imbalance is of a small enough magnitude to be compensated for by the bearing structure mounts 65, without the need for altering the weight of the impeller during assembly.

The lightweight construction also allows for a larger diameter impeller, which in turn provides higher tip speed for a particular RPM. This allows for lower RPM operation of the blower while still achieving the required pressure (which is dependent on tip speed). Having a lower RPM reduces vibration to an acceptable level, or to a level that can be compensated for by the bearing structure and/or stator mount. The lightweight construction of the impeller as mentioned previously enables the larger impeller as it provides lower inertia that achieves the required pressures/response. That is, lower torque is required to speed up and slow down the impeller to reach the required tip speeds/pressures. This improves dynamic performance (response). In addition to this, small magnets in the motor (combined with the bearing structure) remove the need for balancing during assembly, improve dynamic performance.

The resilient/flexible bearing structure allows for self-alignment, compliance, damping and preload of the impeller and shaft assembly. This makes assembly easier, and in combination with the lightweight/low inertia impeller reduce or negates the need for balancing modifications during assembly, as mentioned previously. The bearing structure provides for relaxed tolerances during manufacture as it compensates for larger tolerances. The bearing structure also isolates and/or damps vibrations, also allowing high RPM speeds of the impeller where necessary. The stator frame/motor mount also provides vibration isolation.

The partition that separates the blower into first and second regions separates out the high velocity region to reduce noise. This allows for and maintains a constant high velocity of flow while diffusing the velocity to pressure.

In general, the following advantages are provided for by the combination of one or more features as follows:

| Advantage | Features providing advantage |
|---|---|
| Low noise impeller | Low RPM (due to large diameter impeller) |
| | Partition to provide two regions, one containing the impeller |
| | Low cogging torque |
| | Sensorless vector drive/field oriented control |
| Fast responding blower | Low inertia impeller (achieved through shroudless/lightweight construction) |
| | Small magnet with diameter less than 20 mm |
| | Sensorless vector drive |
| Lower cost | No balancing required during assembly |
| | Small volume magnet |
| | Simple bearing mount |
| | One piece impeller |
| Assembly without balancing | Low inertia impeller/lightweight |
| | Flexible/resilient bearing structure |
| | Motor mount/stator frame isolator |
| | Low RPM impeller |
| | Small magnet with diameter less than 20 mm |
| | One piece impeller |
| Large diameter impeller/ Low RPM | Low inertia impeller |

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

The invention claimed is:

1. A breathing assistance apparatus comprising:
   a pressurised gases source comprising:
      a gases inlet,
      a gases outlet adapted to emit pressurised gases to an outlet of the breathing assistance apparatus,
      a lightweight impeller,
      at least one bearing structure to support a rotatable shaft driving the lightweight impeller, the bearing structure comprising one or more flexible or resilient bearing mounts, the one or more bearing mounts comprising an annular body having an inner surface and an outer surface, the inner surface engaged with one or more bearings and the outer surface engaged with at least one of a stator or a stator frame, wherein the annular body is a curved annular body that curves from a low point at the inner surface to a higher point at the outer surface when the one or more bearing mounts are in an uninstalled or unassembled state, the one or more bearing mounts configured to provide axial preload to the one or more bearings, and
      a housing having a partition defining first and second interior regions within the housing, wherein the first and second regions are fluidly connected by an opening formed in or by the partition.

2. A breathing assistance apparatus according to claim 1 wherein the lightweight impeller is shroudless or otherwise has reduced material.

3. A breathing assistance apparatus according to claim 1 wherein the lightweight impeller is formed in one piece.

4. A breathing assistance apparatus according to claim 1 wherein the lightweight impeller has a radius of between 15 and 60 millimeters.

5. A breathing assistance apparatus according to claim 1 wherein the lightweight impeller has a mass of less than 2 grams.

6. A breathing assistance apparatus according to claim 1 wherein the lightweight impeller has a ratio of pressure compared to inertia to radius of greater than 50:1 Pascal per gram*millimeter.

7. A breathing assistance apparatus according to claim 1 wherein the lightweight impeller has a moment of inertia to radius ratio less than 15 gram*millimeter.

8. A breathing assistance apparatus according to claim 1 wherein the lightweight impeller has a blade sweep volume to a blade volume ratio of 16:1 or greater.

9. A breathing assistance apparatus according to claim 1 wherein the lightweight impeller is a centrifugal impeller rotatable about a central axis.

10. A breathing assistance apparatus according to claim 1 further comprising a motor for driving the lightweight impeller wherein the motor is operated using field oriented control.

11. A breathing assistance apparatus according to claim 1 wherein the housing has upper and lower internal surfaces that enclose the lightweight impeller, and wherein the lightweight impeller has a plurality of blades that are substantially open to the upper and lower internal surfaces of the housing by virtue of being shroudless.

12. A breathing assistance apparatus according to claim 11 wherein the housing forms part of or is integrated with the breathing assistance apparatus.

13. A breathing assistance apparatus according to claim 1 wherein the opening formed in or by the partition is at least partially circumferential.

14. A breathing assistance apparatus according to claim 1 wherein the first region is defined by the housing and the partition and comprises the gases inlet.

15. A breathing assistance apparatus according to claim 1 wherein the second region is defined by the housing and the partition and comprises the gases outlet.

16. A breathing assistance apparatus according to claim 1 wherein the lightweight impeller has an axis of rotation, the partition extending radially from the axis of rotation.

17. A breathing assistance apparatus according to claim 1 wherein the housing further comprises a volute in the second region.

18. A breathing assistance apparatus according to claim 17 wherein the volute has a tongue at least partially defining a transition between the volute and the gases outlet, the tongue located in the second interior region.

19. A breathing assistance apparatus according to claim 1 wherein the opening is proximate the periphery of a volute.

20. A breathing assistance apparatus according to claim 1 wherein the lightweight impeller is located within the first region.

21. A breathing assistance apparatus according to claim 1 wherein a distal end of impeller blades of the lightweight impeller curve in the direction of blade rotation.

22. A breathing assistance apparatus according to claim 1 wherein the one or more bearing mounts provide compliant support to the rotatable shaft.

23. A breathing assistance apparatus according to claim 1 wherein the breathing assistance apparatus further comprises a motor, the motor comprising the rotatable shaft located within a stator and supported by the at least one bearing structure.

24. A breathing assistance apparatus according to claim 23 wherein an outer portion of the one or more bearing mounts engages at least one of the stator or the stator frame.

25. A breathing assistance apparatus according to claim 23 wherein the stator comprises a stator frame, and an inner surface of the stator frame engages with the at least one bearing structure.

26. A breathing assistance apparatus according to claim 23 wherein the pressurised gases source has a housing and the breathing apparatus further comprises a motor mount that couples the stator and the housing to provide compliant support to the motor.

27. A breathing assistance apparatus according to claim 26 wherein the motor mount is flexible or resilient.

28. A breathing assistance apparatus according to claim 1 wherein the at least one bearing structure further comprises one or more bearings supported by the one or more bearing mounts about the axis of the rotatable shaft.

29. A breathing assistance apparatus according to claim 28 wherein the one or more bearing mounts provide the axial preload to the one or more bearings when the annular body is coerced into an engaged configuration.

30. A breathing assistance apparatus according to claim 29 wherein the one or more bearing mounts are made from a material that provides resilience or flexibility to provide the axial preload when in the engaged configuration.

31. A breathing assistance apparatus according to claim 1 wherein the one or more bearing mounts are made from a material that provides damping.

32. A breathing assistance apparatus according to claim 1 wherein the one or more bearing mounts are configured to provide the axial preload to the one or more bearings of up to 7 Newtons.

33. A breathing assistance apparatus according to claim 1 wherein an inner annular wall extends upwards from the annular body at the inner surface.

34. A breathing assistance apparatus according to claim 33 wherein a top portion of the inner annular wall has an overhanging engagement lip, wherein, when engaged, the overhanging engagement lip is configured to be positioned adjacent a top surface of the one or more bearings.

35. A breathing assistance apparatus according to claim 1 wherein at the outer surface comprises an engaging lip at an intersection of the outer surface with the annular body.

36. A breathing assistance apparatus comprising:
 a pressurised gases source comprising:
  a housing,
  a gases inlet,
  a gases outlet adapted to emit pressurised gases to an outlet of the breathing assistance apparatus,
  a motor with a rotatable shaft and at least one bearing structure to support the rotatable shaft within a stator, the bearing structure having one or more flexible or resilient bearing mounts to provide at least one of compliance, axial preload, or damping for the rotatable shaft, the one or more bearing mounts comprising an annular body having an inner surface and an outer surface, the inner surface engaged with one or more bearings and the outer surface engaged with the stator, wherein the annular body is a curved annular body that curves from a low point at the inner surface to a higher point at the outer surface when the one or more bearing mounts are in an uninstalled or unassembled state,
 a lightweight impeller coupled to the rotatable shaft,
 a flexible or resilient motor mount that couples the stator and the housing to provide at least one of compliance or damping for the motor, and
 a partition to define first and second interior regions within the housing, wherein the first and second regions are fluidly connected by an opening formed in or by the partition.

* * * * *